(12) United States Patent
Vilasi et al.

(10) Patent No.: US 9,010,332 B2
(45) Date of Patent: Apr. 21, 2015

(54) EXPANDABLE INTER VIVOS TUBE

(71) Applicants: Joseph A. Vilasi, Lakewood Ranch, FL (US); Joseph D'Ambrosio, Ridgefield, CT (US)

(72) Inventors: Joseph A. Vilasi, Lakewood Ranch, FL (US); Joseph D'Ambrosio, Ridgefield, CT (US)

( * ) Notice: Subject to any disclaimer, the term of this patent is extended or adjusted under 35 U.S.C. 154(b) by 0 days.

(21) Appl. No.: 14/300,234

(22) Filed: Jun. 10, 2014

(65) Prior Publication Data

US 2014/0345622 A1 Nov. 27, 2014

Related U.S. Application Data

(63) Continuation-in-part of application No. 14/231,541, filed on Mar. 31, 2014, which is a continuation of application No. 13/662,552, filed on Oct. 29, 2012, now abandoned, application No. 14/300,234, which is a continuation-in-part of application No. 14/228,891, filed on Mar. 28, 2014, which is a continuation-in-part of application No. 13/662,552, filed on Oct. 29, 2012, now abandoned, application No. 14/300,234, which is a continuation-in-part of application No. 14/109,880, filed on Dec. 17, 2013, which is a continuation-in-part of application No. 13/662,552, filed on Oct. 29, 2012, now abandoned.

(51) Int. Cl.
*A61M 16/00* (2006.01)
*A61M 16/04* (2006.01)
*A61M 16/08* (2006.01)
*A61M 25/10* (2013.01)

(52) U.S. Cl.
CPC ....... *A61M 16/0477* (2014.02); *A61M 16/0418* (2014.02); *A61M 16/0434* (2013.01); *A61M 16/0816* (2013.01); *A61M 25/1025* (2013.01); *A61M 16/0465* (2013.01); *A61M 16/0497* (2013.01); *A61M 16/0445* (2014.02)

(58) Field of Classification Search
USPC ........... 128/200.26, 207.14–207.15, DIG. 20; 604/96.01, 99.01–99.03, 104–105; 623/9; 138/156–158, 162, 167
See application file for complete search history.

(56) References Cited

U.S. PATENT DOCUMENTS

| | | | |
|---|---|---|---|
| 5,647,358 A | 7/1997 | Vilasi | |
| 6,408,850 B1 | 6/2002 | Sudge | |
| 2008/0115789 A1 | 5/2008 | Green | |
| 2010/0313894 A1 | 12/2010 | Crumback | |
| 2010/0313896 A1* | 12/2010 | O'Neil et al. | 128/207.15 |
| 2011/0048427 A1* | 3/2011 | Zachar | 128/207.15 |

* cited by examiner

*Primary Examiner* — Rachel Young
*Assistant Examiner* — Timothy Stanis
(74) *Attorney, Agent, or Firm* — Law Office of Carl Giordano, PC.

(57) ABSTRACT

A flexible expandable inter vivos tube includes at least one arched segmented portion, a corresponding movable element and at least one positioning mechanism. The at least one arched segmented portion and corresponding movable element forming a flexible closed longitudinally expandable tube. The at least one arched segment includes an H-shaped connector having at least one cavity that allows variable slidable movement of a free end portion of the corresponding movable element. A flexible membrane is contained in the at least one cavity so that the hydraulic or air pressure within an inner rib of the H-shaped connector expands the movable element and, thus, the circumference of the flexible inter vivos tube are increased. The flexible membrane attached to the free end portion limits the travel of the movable element within a corresponding one of the at least one cavity.

20 Claims, 23 Drawing Sheets

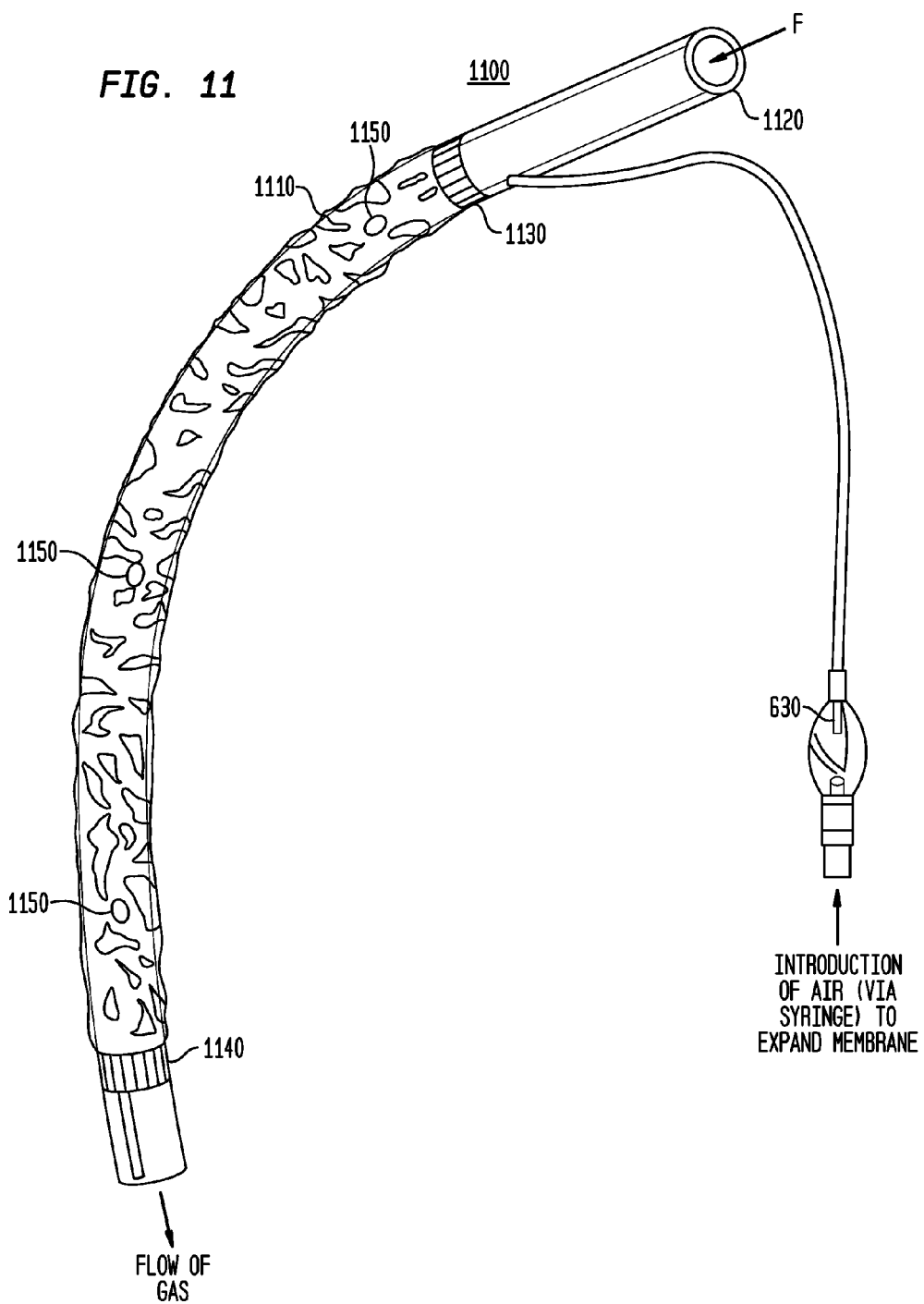

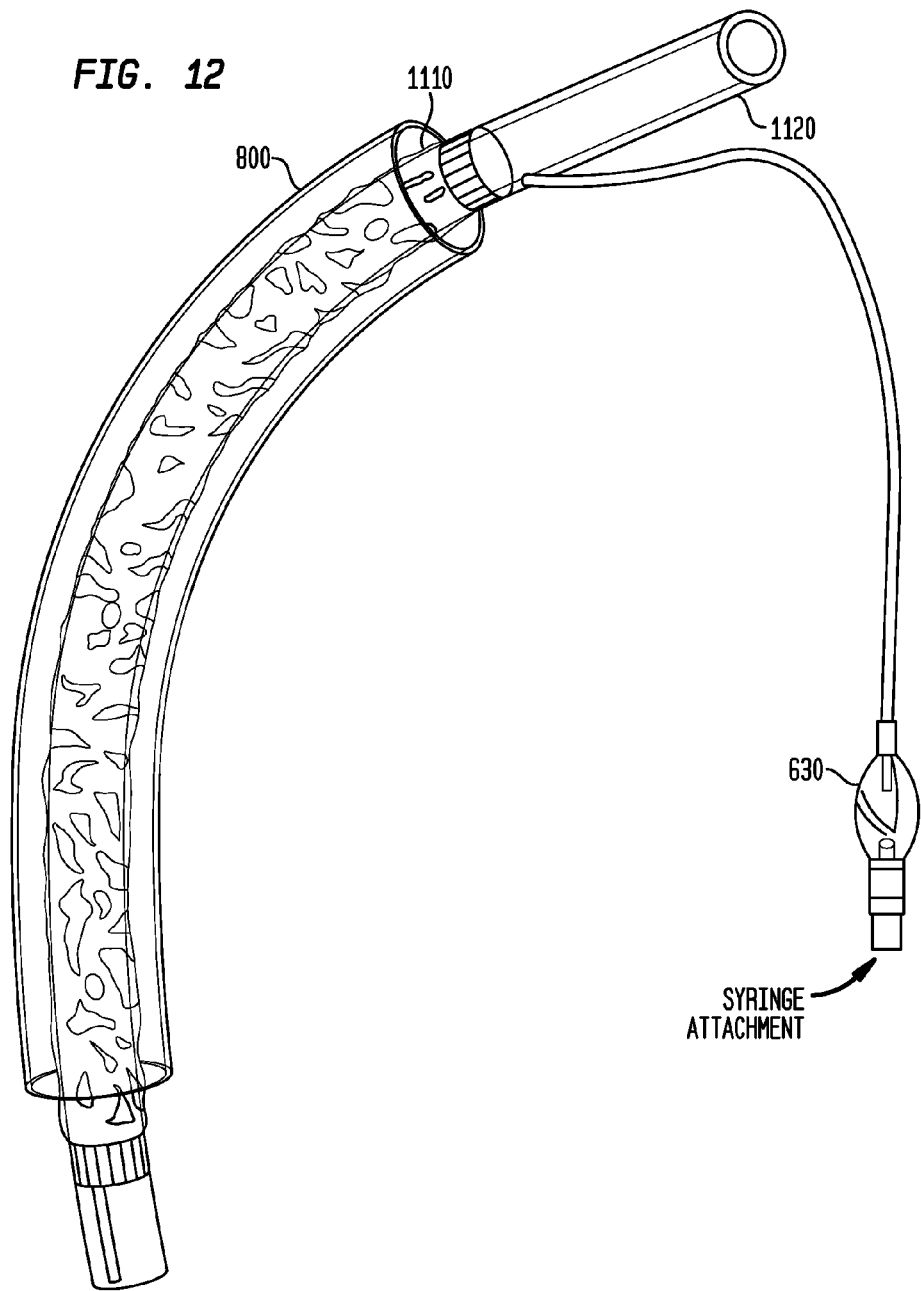

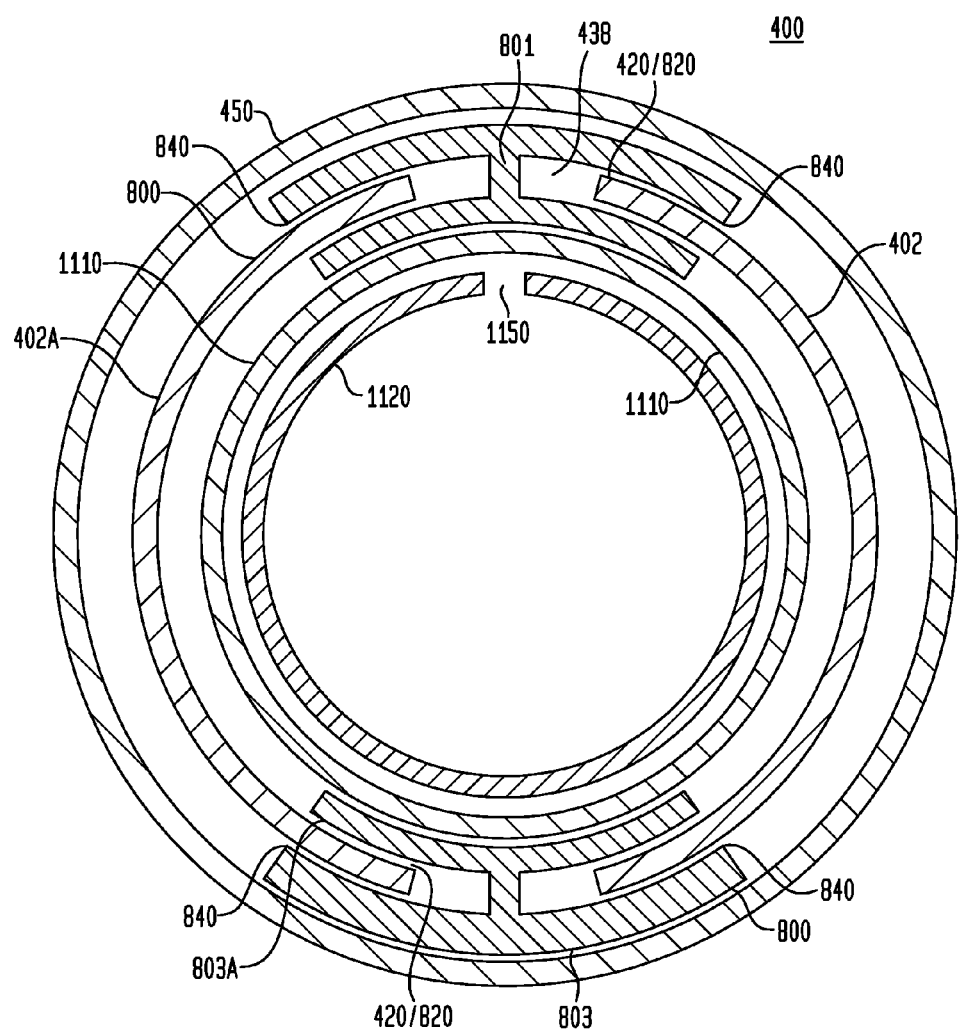

1400

EXPANDABLE INTER VIVOS TUBE

CLAIM OF PRIORITY

This application claims, pursuant to 35 USC 120, as a continuation-in-part, the benefit of the earlier filing date of, and priority to that application entitled, "Expandable Inter Vivos Tube," filed on Mar. 31, 2014 and afforded Ser. No. 14/231,541 (JVilasi-001CON-1), which claimed, pursuant to 35 USC 120, as a continuation, the benefit of the earlier filing data of and priority to that patent application entitled "Expandable Inter Vivos Tube," filed in the US Patent and Trademark Office on Oct. 29, 2012 and afforded Ser. No. 13/662,552 (JVilasi-001), and further claims, pursuant to 35 USC 120, as a continuation-in-part, the benefit of the earlier filing data of, and priority to, that patent application entitled "Expandable Inter Vivos Tube," filed on Mar. 28, 2014 (JVilasi-003) and afforded Ser. No. 14/228,891, which claimed, pursuant to 35 USC 120, as a continuation-in-part, the benefit of the earlier filing data of and priority to that patent application entitled "Expandable Inter Vivos Tube," filed in the US Patent and Trademark Office on Oct. 29, 2012 and afforded Ser. No. 13/662,552 (JVilasi-001), and further claims, pursuant to 35 USC 120, as a continuation-in-part, the benefit of the earlier filing data of, and priority to, that patent application entitled "Expandable Inter Vivos Tube," filed on Dec. 17, 2013 (JVilasi-002) and afforded Ser. No. 14/109,880, which claimed, pursuant to 35 USC 120, as a continuation-in-part, the benefit of the earlier filing data of and priority to that patent application entitled "Expandable Inter Vivos Tube," filed in the US Patent and Trademark Office on Oct. 29, 2012 and afforded Ser. No. 13/662,552 (JVilasi-001), the contents of all of which are incorporated by reference herein.

BACKGROUND

1. Field of the Invention

The present invention relates to the field of medical devices and, more particularly, to an expandable tube for inter vivos.

2. Background of the Invention

Inter vivos tubes, such as endotracheal tubes, are used to provide gases to the lungs during surgery. For example, an endotracheal tube is inserted into the trachea with its distal tip advanced halfway toward the tracheal bifurcation to provide gases, such as oxygen and anesthetics to a patient during surgery. The exposed portion of the endotracheal tube is then firmly taped to the patient's face to prevent undesirable movement.

To align the position of conventional endotracheal tubes, an inflatable cuff balloon, at the distal end of the endotracheal tube, is inflated to correspond to the inner diameter of a portion of the trachea, thereby centering, or otherwise positioning, the endotracheal tube within the trachea. The cuff balloon, however, does not completely obstruct the entire trachea; only the portion where it is anchored is obstructed. When the cuff balloon is inflated, confirmation of the expanded balloon's contact within the trachea is achieved and delivery of anesthetic gases is performed.

Because of various sized endotracheal tubes, it is preferable to at least make the outer diameter of the endotracheal tube closely proximate to the size of the glottis, or opening between the vocal cords, for selective positioning of the endotracheal tube at a predetermined dilation. Therefore, various sized tubes are used, and the anesthesiologist or nurse anesthetist must choose from a variety of sized tubes to insert in the patient. If nasotracheal intubation or tracheostomy tubes are required in present practice even smaller interior diameters (ID) tubes are used.

Conventional endotracheal tubes vary in size and are numbered according to an internal diameter (ID). For example, for children, tubes are measured at about 3.5 to 7 mm (millimeters) internal diameter and from 7 to 11 mm for an adult. The internal diameter in women varies in general from 7.0 to 8.5 mm ID and in men from 8 to 10 mm ID. Typically, an endotracheal tube size selected for each patient is empirically selected by the anesthesiologist based on the patient's gender, age and size.

Ideally, the endotracheal tube should approximate as closely as possible the glottic size of the patient. Since there is no way to estimate the glottic size prior to the administration of anesthesia, in the existing prior art endotracheal tubes, a distal inflatable cuff is incorporated into the present day endotracheal tube which, when inflated, compresses the tracheal wall, thus creating a closed circuit between the endotracheal tube inflow from the anesthesia machine and outflow from the patient's lung to the exhalation valve. When nasotracheal intubation or tracheostomies is necessary, the internal diameter of the endotracheal tube is even less than the normal sizes, which are selected for orotracheal intubation, even greater respiratory resistance is created.

Furthermore, as noted in "Clinical Anesthesia", 1989 Edition, J. B. Lippincott Company, edited by Paul Barash, MD, Bruce Cullen, MD, and Robert Stoelting, MD, "[e]ndotracheal tube resistance varies inversely with the tube size. Each millimeter decrease in tube size is associated with an increase in resistance of 25 ro100%. The work of breathing parallels changes in resistance. A one (1) mm decrease in tube size increases the work of breathing from 34 to 154%, depending on the ventilatory pattern".

Therefore, in existing prior art inter vivos tubes, the internal diameter is small, and the only large portion is the external cuff balloon. This makes it harder for a surgical patient to breathe through the small internal diameter of the existing endotracheal tubes, especially if the patient must breathe spontaneously without assistance.

In summary, the prior art uses a local, inflatable balloon at the distal portion of an endotracheal tube, which narrows the patient's air way at the vocal cord level and may damage the vocal chords of the patient, if not property installed.

Applicant's prior U.S. Pat. No. 3,968,800 dated Jul. 13, 1976 and U.S. Pat. No. 4,827,925 dated May 9, 1989 describe an adjustable endotracheal tube which is complex to expand, and which does not have flexibility in being adapted to varying sized tracheas of different patients. Applicant's other prior U.S. Pat. No. 4,722,335 dated Feb. 2, 1988 discloses an expandable endotracheal tube including two overlapping curved segments, which when joined together form a closed tube. Similarly, applicant's prior U.S. Pat. No. 5,647,358, dated Jul. 15, 1997, discloses an expandable inter vivos tube that provides for expansion of the tube along at least designated parts of the tube. However, the configuration may be conceptually possible but in practical terms, difficult to construct and maintain at present prices.

Hence, there is a need in the industry for an expandable inter vivos tube that is easy to construct, easy to install, expand and remove during a procedure while reducing construction and costs of construction.

SUMMARY OF THE INVENTION

It is therefore an object of the present invention to provide a flexible, expandable inter vivos tube that expands its internal diameter at the glottic region of the trachea, to make breathing easier for a surgical patient.

Another object of the flexible, expandable inter vivos tube of the present invention is to vary a size of the internal diameter (ID) of an endotracheal tube in order to reach the glottic size of the patient without the intervention of a distal inflatable cuff.

With the present invention, the distal cuff is unnecessary and the one size endotracheal tube would fit most all adult patients. The present invention is especially useful in nasotracheal intubations where normally an even smaller internal diameter tube would be selected by the anesthesiologist.

It is also an object of the present invention to provide an endotracheal tube that maintains the same wall thickness throughout, without tapering.

It is yet another object of the present invention to provide an inter vivos tube having an internal diameter that remains substantially consistent from a proximal end to a distal end.

Another object of the present invention is to provide a vessel for administration of anesthesia by means of a flexible expandable tube that can be positioned correctly without interrupting gas flow and/or organ activity of a surgical patient.

It is also an object of the invention to provide a tube that can operate as an artificial flexible expandable vessel, such as a segment of a blood vessel to replace clogged arteries, or as a permanent catheter duct for providing fluids to or from the body.

It is also an object of the present invention to provide an improved inter vivos tube that overcomes the disadvantages of the existing prior art expandable tubes.

The basic concept of the present invention is to equip an inter vivos vessel, such as an endotracheal tube, artificial blood vessel or other tube with a positioning mechanism that is activated from a proximal end of the vessel and allows exact positioning and reversible anchoring within a body cavity, such as the trachea. The expandable tubes discloses herein can also be utilized as esophageal dilators, laparoscopic tubes, etc.

In the endotracheal tube embodiment, exact positioning and anchoring provide the conditions to provide anesthetic gases at the target, namely to the bronchial tubes, and ultimately the lungs.

In the present invention, the endotracheal tube can be anchored in the internal diameter of a body cavity, such as the trachea. The tube is expanded in size by means of an axially and longitudinally extendable elements inserted within the opposite free ends of a cul-de-sac formed by an H-like element. The extendable member includes free ends that run substantially the longitudinally length of the intro vivos tube. The two free edges of the extendable (flexible) cylindrical body elements engage corresponding free ends of the H-shaped element, which is curved to complete the circumference of the flexible expandable endotracheal tube. The "H" segment also provides for the integrity of the tube and, is constructed of a more rigid plastic than the rest of the tube itself. The remainder of the endotracheal tube utilizes the same or similar semi-rigid materials used in conventional inter vivos tubes. Polyvinyl tubes are presently used and continue to be used with varying degrees of hardness.

Moreover, upon extubation of the inter vivos tube of the present invention, retraction of the diameter of the tube is not required. By axially shifting the segmented arches away from each other at the free ends of the tube within the cul-de-sac of the "H" shaped element, the segmented arches are expanded so that the size of the endotracheal tube is increased and anchored during the administration of anesthesia. The segmented arches can be spread axially and longitudinally away from each other by injecting gas (or air) or fluid such as (saline) with a syringe connected to a one way valve and tube inserted in the lumen of a longitudinal canal within the rib of the "H".

The free ends of the flexible interrupted cylindrical tube are axially and longitudinally displaced away from each other so that the internal diameter of the endotracheal tube is expanded to anchor the tube within a body cavity, such as the trachea. One or more entry points may be used to provide fluid or air within a selected longitudinally extending rib of the "H" like element. The entry point(s) are also within a canal location in the wall on the expandable tube.

The longitudinal rib within the "H" is pierced at two or more levels along the course of the "H" element in order to distribute the gas or fluid to substantially the length of the tube substantially uniformly.

It is important to note an expandable membrane is sealed to the inner and outer surfaces of the "H" element and also completely surrounds the free ends of the H-shaped element. However, the portion of the membrane that surrounds the free arms of the "H" will allow the opposite free longitudinal ends of the endotracheal tube to remain inserted within the cul-de-sac formed by the free arms of the "H" element. When air or fluid is injected into a longitudinal channel within a rib of the "H", the two free ends of the endotracheal tube will slide substantially evenly apart to a desired expansion.

In another aspect of the invention, an optional non-expandable membrane can be fused along the entire length of the outer part of the "H" element and on the two expanding arms of the endotracheal tube longitudinally at a distance away from the free arms of the "H" element equal to the depth of the cul-de-sac. In this manner the tube cannot over expand.

In another aspect of the invention, the entire endotracheal tube can, itself, be sealed by a condom-like membrane to maintain smoothness and to help maintain the integrity of the tube itself.

According to an embodiment of the invention, the free end of one side of the cylindrical body, or segmented arch, can be moved, and the opposite side would be firmly attached inside the other free end of the H-shaped element. By means of the self-acting spreading of the endotracheal tube after insertion, the position of the endotracheal tube is maintained so that controlled anesthesia can be performed without gas regurgitation.

In another embodiment of the invention, the free ends of the "H" element may include a retaining or locking point that engages saw-tooth means or serrations in the extendable elements inserted within the free ends of the cul-de-sac formed by the "H" element. The engagement of the retaining point of the free-end of the "H" element and the serrations in the extendable elements lock the extendable element in an extended position.

In this embodiment of the invention, an expandable tube (referred to as an expander tube) may be inserted into the inter vivos tube in order to expand the extendable elements of the inter vivos tube to a desired position. The expander tube may then be removed after a desired expansion of the inter vivos tube is achieved. The expander tube may be reused, if desired, after sterilization.

In another embodiment of the invention, the retaining point of the free end of the "H" element may be hinged to lock the extendable elements to remain in the expanded mode.

In one embodiment of the invention, an inter vivos system is disclosed which comprises an expandable inter vivos tube comprising: a longitudinal H-shaped member comprising: an arched outer member; an arched inner member; a rib member connecting, at a substantial midpoint of said arched outer member and said arched inner member, said arched outer member, said arched inner member and said rib member forming first and second cavities, respectively; a retaining pin positioned on a free end of one of said arched outer member and said arched inner member, said retaining pin projecting into an opening of a corresponding one of said first and second cavities, and a flexible tube split along a longitudinal axis, said split forming first and second free ends, said first and second free ends engaging corresponding ones of said first and second cavities, wherein each of said first and second free ends include at least one serration, said at least one serration engaging said retaining pin, wherein flexible tube and said arched outer member having a radius forming said inter vivos tube with a substantially circular cross-section; and an expansion means comprising: a hollow tube member including a plurality of egress points along a longitudinal axis of said tube; and an expandable member attached to said proximate end and to said distal end of said tube member; wherein said tube member is sized to fit within an inner diameter of said expandable inter vivos tube.

The inter vivos tube of the present invention, advantageously, expands substantially uniformly along its entire axial length, as fluid or air is pumped from a syringe into expansion lumens within the rib of the "H" or by the insertion of an expander tube.

BRIEF DESCRIPTION OF THE DRAWINGS

The advantages, nature, and various additional features of the invention will appear more fully upon consideration of the illustrative embodiments to be described in detail in connection with accompanying drawings wherein like reference numerals are used to identify like element throughout the drawings:

FIG. 11 illustrates a first mode of an expansion means for expanding the inter vivos tube shown in FIG. 8.

FIG. 12 illustrates an expandable inter vivos tube in an expanded mode including expansion means shown in FIG. 11.

FIGS. 13A and 13B illustrate a cross sectional views of the inter vivos tube including the expansion means in accordance with the principles of the invention.

It is noted that the drawings of the invention are not to scale. The drawings are intended to depict only typical aspects of the invention, and therefore should not be considered as limiting the scope of the invention. In the drawings, like numbering represents like elements between the drawings.

It is to be understood that the figures and descriptions of the present invention described herein have been simplified to illustrate the elements that are relevant for a clear understanding of the present invention, while eliminating, for purposes of clarity many other elements. However, because these elements are well-known in the art, and because they do not facilitate a better understanding of the present invention, a discussion of such element is not provided herein. The disclosure herein is directed to also variations and modifications known to those skilled in the art.

DETAILED DESCRIPTION OF THE PRESENT INVENTION

Figure 1:
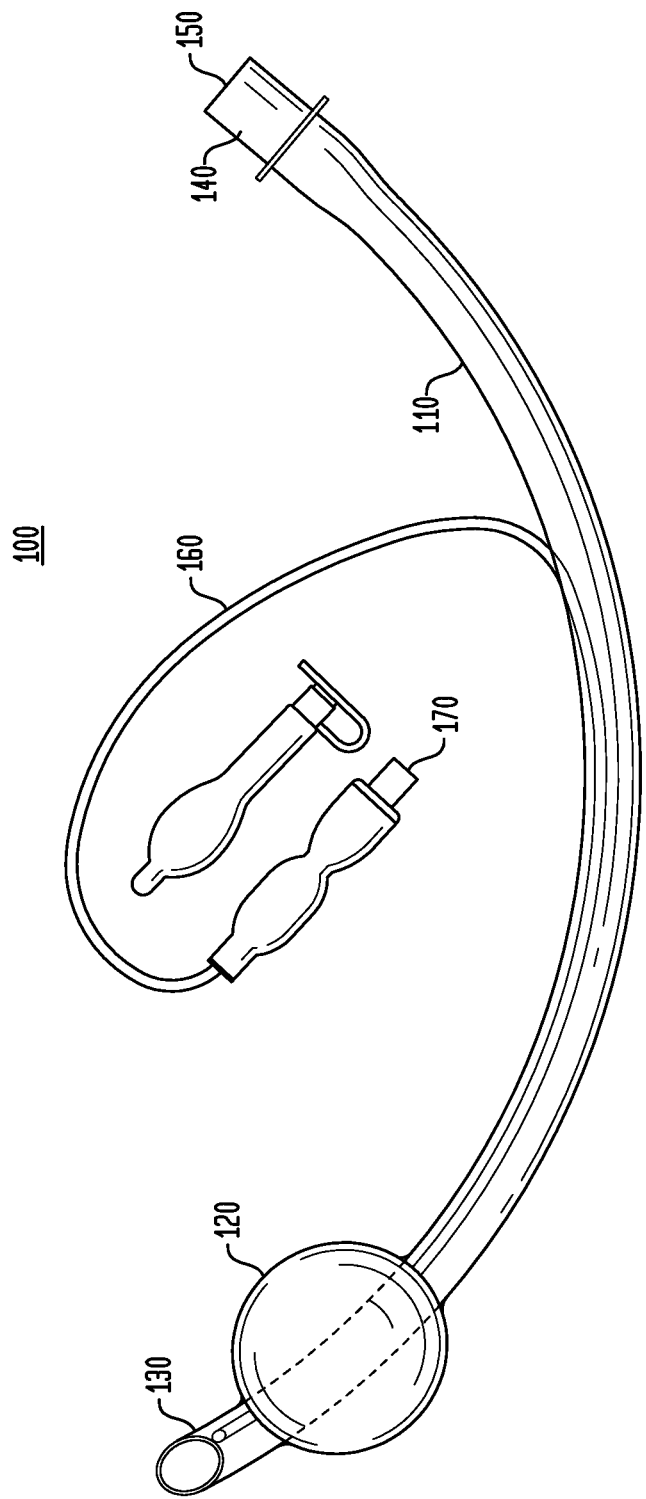
FIG. 1 illustrates a prospective view of conventional endotracheal tube with an expanded distal cuff which compresses distally against the tracheal wail.

FIG. 1 illustrates a conventional endotracheal tube (i.e., inter vivos tube) 100 represented as an elongated tube 110 having a bulb member 120 positioned on a distal end 130 and a connection member 140 on a proximate end 150. The connection member 140 on proximate end 150 provides a means for allowing gases to flow through inter vivos tube 100 to distal end 130. Bulb member 120, which is shown in an expanded position, seals a passageway (not shown) into which inter vivos tube 100 is inserted to prevent gases exiting the distal end 130 from escaping along the inter vivos tube 100.

FIG. 1 further illustrates a smaller tube 160 running along an inner edge of inter vivos tube 100. Tube 160 may be used to provide a fluid, e.g., air or liquid, to bulb member 120 so as to expand bulb member 120 to the illustrated inflated position. Tube 160 may be connected to an air or liquid supply (not shown) by connection member 170.

Figure 2:
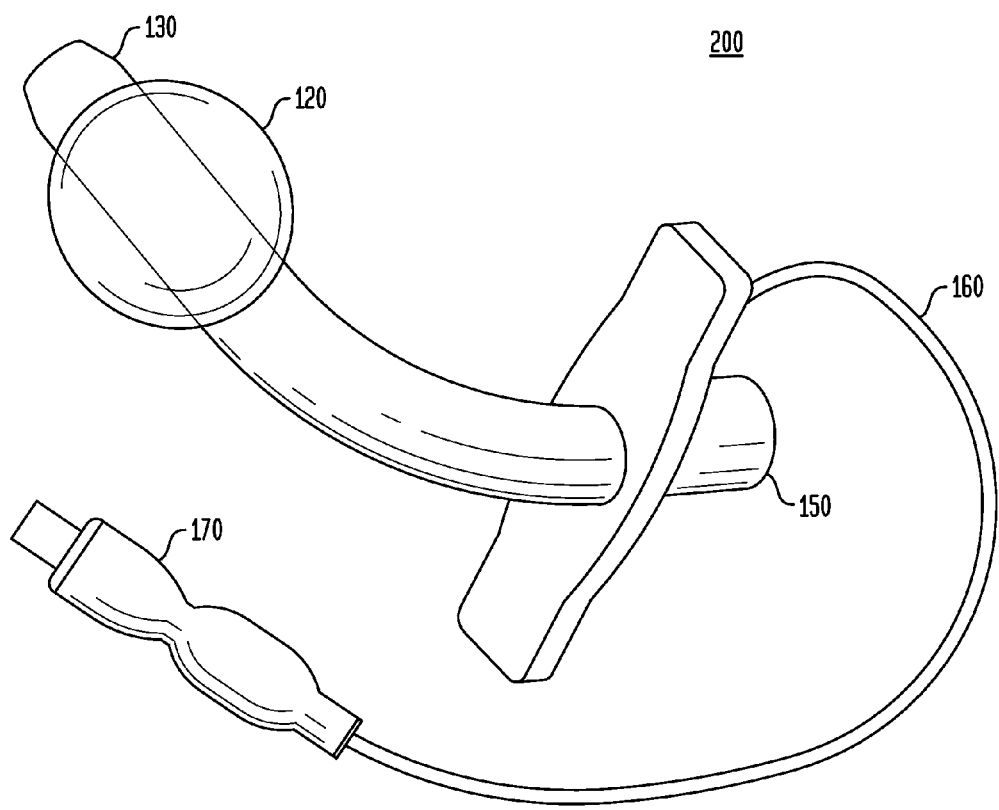
FIG. 2 illustrates a prospective view of a conventional tracheostomy tube inflated distally in the same manner, as in FIG. 1.

FIG. 2 illustrates a conventional tracheostomy tube (i.e., inter vivos tube) 200 used in providing air to a patient undergoing a tracheostomy process. Inter vivos tube 200 operates in a manner similar to that of the inter vivos tube 100 shown in FIG. 1, wherein a bulb member 120, positioned at a distal end 130, is expanded to prevent a fluid (e.g., air or liquid) injected from the proximate end 150 from escaping along the inter vivos tube 200. A fluid, such as air or liquid, enters through connection member 170 to expand bulb member 120, as previously discussed.

Figure 3:
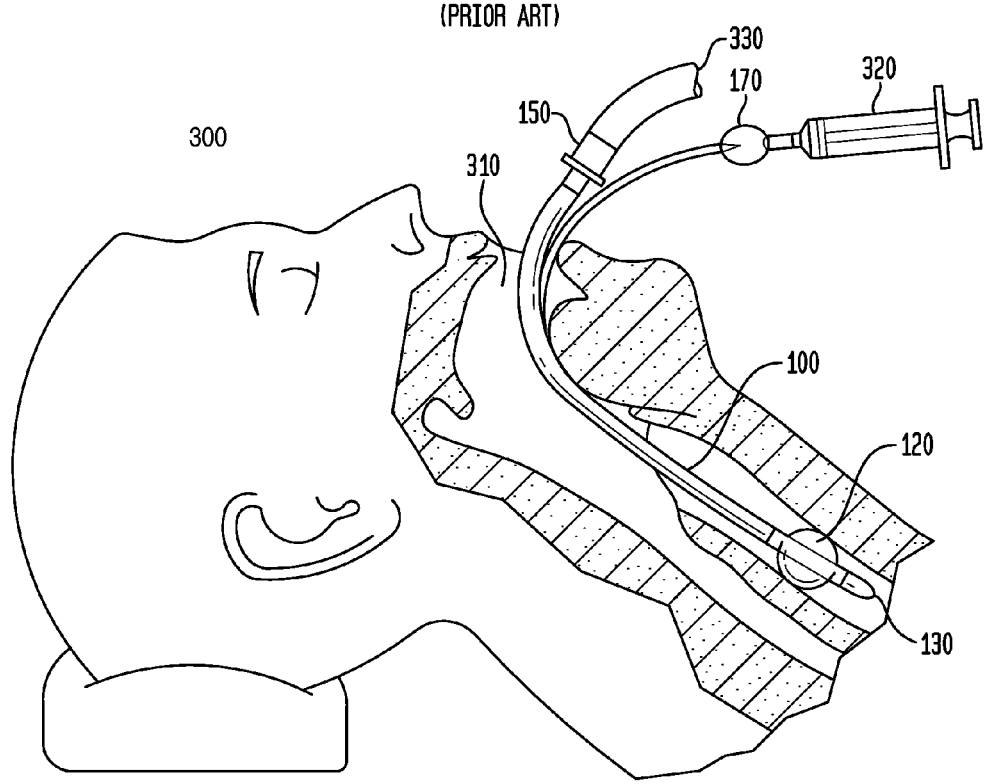
FIG. 3 illustrates a prospective view of a conventional endotracheal tube inserted through the vocal cords and expanded within the trachea.

FIG. 3 illustrates a cross-sectional view 300 of the insertion and positioning of a conventional endotracheal tube 100 through a patient's vocal cords. As shown, bulb member 120 is an expanded mode to seal the patient's air passage 310. Also shown is syringe 320 that is connected to connection member 170 that represents a means for providing fluid to bulb member 120 so as to expand bulb member 120 to seal air passage 310. Also shown is tube 330 that is connected to connection member 170 to allow a fluid (e.g., gas, air, liquid) to pass from proximate end 150 of the inserted endotracheal tube 100 to distal end 130 of the inserted endotracheal tube 100.

Figure 4A:
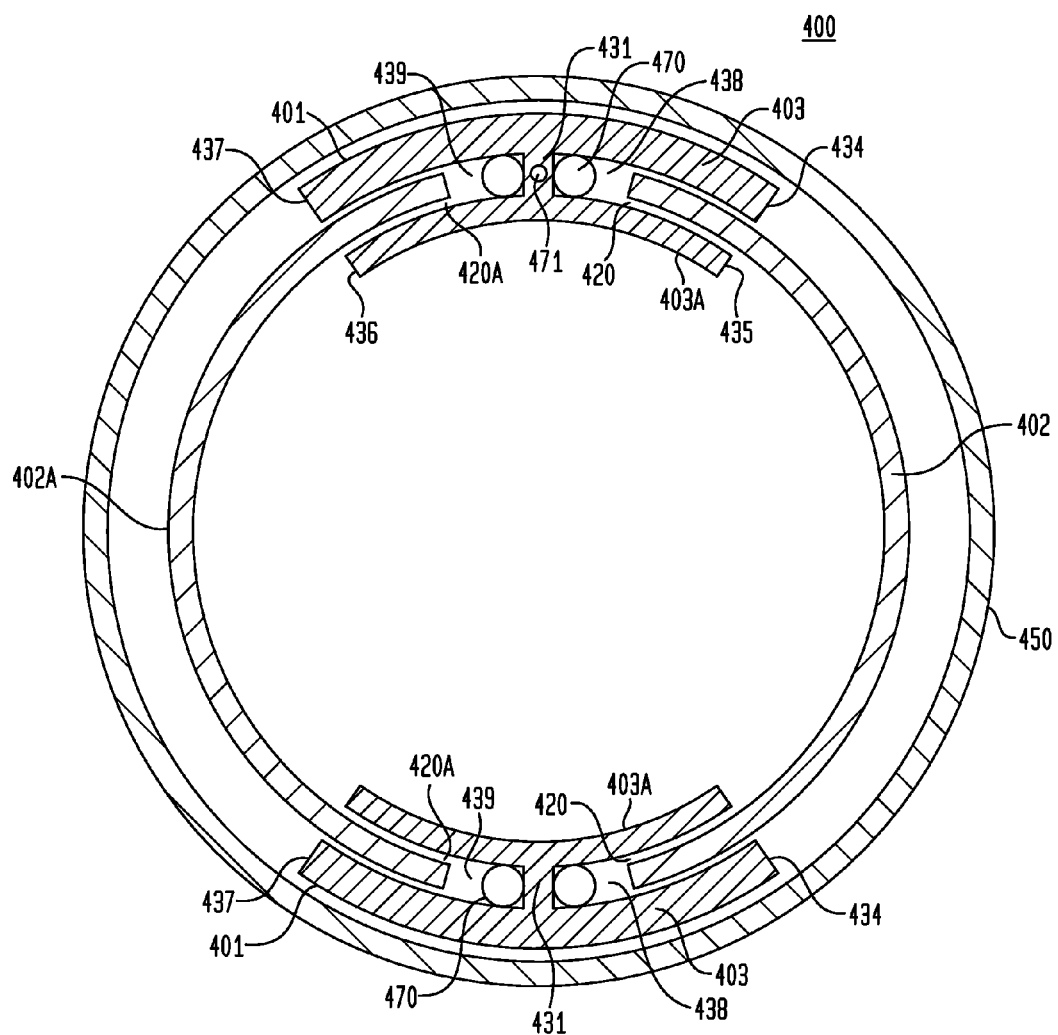
FIGS. 4A and 4B illustrates cross-sectional views of a first and second aspect of inter vivos tubes in accordance with the principles of the invention.

FIG. 4A illustrates a cross-sectional view of an exemplary inter vivos tube 400 in accordance with the principles of the invention. As shown, inter vivos tube 400 includes two (2) H-shaped connector elements 401 opposite to each other and extending substantially longitudinally along an edge of inter vivos tube 400. Each of the H-shaped connector elements 401 comprises an arched outer element 403 (outer circumference element) and an arched inner element 403A (inner circumference element) arranged circumferentially opposite each other at equal angles to each other along a circumference of the flexible expandable inter vivos tube 400. The H-shaped connection 401 includes rib 431, which represents the crossbar of the "H" in the H-shaped connection member 401 joining at a substantial midpoint of the arched elements 403 and 403A. The H-shape connector elements 403 and 403A, taken with rib 431, also form cul-de-sac receptacle cavities 438 and 439, respectively. The cul-de-sac cavities 438 and 439 have an opening that is sized to receive, in tongue-in-groove-like fashion, free end tongue portions 420 and 420A of arched tube segments 402 and 402A, respectively. The H-shaped connector member 401 has respective free ends 434, 435 that define cavity 438 and free ends 436 and 437 that define cavity 439. Outer curved or ached element 403 is longer than inner curved arched element 403A to accommodate an increase in circumference.

Rib 431 connects the arched elements 403, 403A of each H-shaped connector member 401 and provides rigidity and structural integrity for the inter vivos tube 400. The rigidity of rib 431 has sufficient flexibility to enable the inter vivos tube 400 to be inserted into the trachea of the patient and to conform to the patient's airway, while retaining sufficient rigidity to permit a medical worker to position and to insert the tube 400 against anatomical resistance of the patient's throat and airway structures. Rib 431 may also include longitudinal conduit 471 for accepting a fiber optic cable for view-0-scope enablement.

The H-shaped connector member may be made of a material such as polyvinyl chloride plastic, to provide sufficient rigidity and flexibility.

Tongues 420 (420A) of arched tube elements 402, 402A, respectively, are normally in a retracted position within corresponding cavities 438, 439, providing inter vivos tube 400 with a minimum diameter.

Although not shown, it would be appreciated that the diameter of inter vivos tube 400, along an axis substantially perpendicular to the arched tube elements 402, increases when tongues 420 (420A) are forced circumferentially apart by entrance of a fluid pumped into the respective cavities 438, 439. Hence, the cross sectional profile of the inter vivos tube in accordance with the principles of the invention is one of substantially circular in an unexpanded mode and of an elliptical in an expanded mode.

The increased diameter of the inter vivos tube 400, caused by the displacement of the tongue elements 420 (420A) of corresponding arched segments 402, 402A causes the passageway (FIG. 3, 310) into which the inter vivos tube 400 is inserted to become blocked, such that air may only enter or exit the passageway through the internal diameter formed by the inter vivos tube 400.

In addition, the cavities 438, 439 and tongues 420 (420A) are sized to prevent tongues 420 (420A) from expanding to a distance that would cause tongues to exit cavities 438, 439.

Also, shown is an, optional, expandable membrane 450 that surrounds inter vivos tube 400. Optional membrane 450 may be composed of a material that provides for a smooth surface of the inter vivos tube 400. The optional membrane 450 may be composed of a material such as PVC (polyvinyl chloride) that allows for a smooth entry and exit of the inter vivos tube 400 into and out of a passage way (e.g., FIG. 3, 310).

In a second exemplary aspect of the invention, flexible membranes 470 may be incorporated into cavities 438, 439. Flexible membranes 470 may expand as fluid (gas, air, liquid) is injected into H-shaped connection member 401.

Figure 4B:
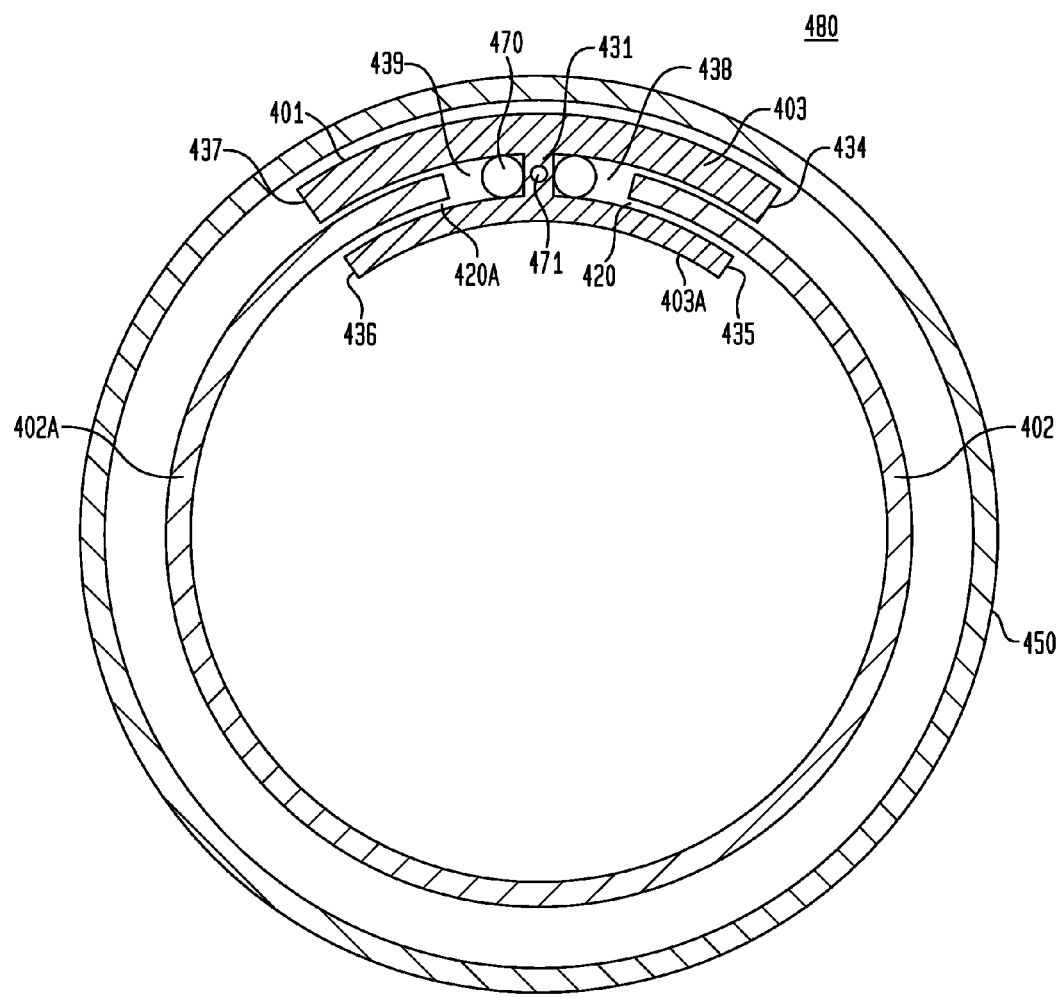

FIG. 4B illustrates a second aspect of an inter vivos tube 480, which is similar to the inter vivos tube 400 shown in FIG. 4A. In this second aspect of the invention, a single H-shaped connection member 401 is incorporated into the inter vivos tube 480. As the elements of the single H-shaped member 401 shown in inter vivos tube 480 are the same as those of the H-shaped connector member 401 described with regard to FIG. 4A, a detailed description of H-shaped member 401 shown in FIG. 4B need not be repeated again herein.

In this exemplary second aspect, and as previously described, a diameter of the inter vivos tube 480 increases in a direction substantially perpendicular to arched segments 402, 402A as tongues 420 (420A) are displaced from cavities 438, 439 as a fluid (or air) is injected into the H-shaped connector members 401, as previously described.

Figure 5A:
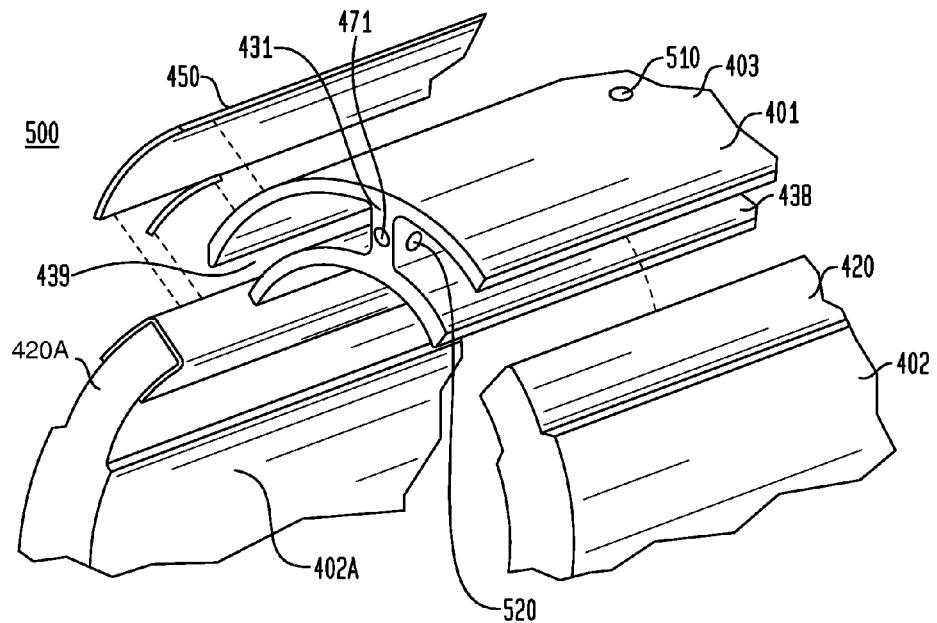
FIGS. 5A and 5B illustrate prospective exploded views of inter vivos tubes in accordance with a first embodiment of the invention.

FIG. 5A illustrates an expanded prospective view of the inter vivos tube 400 shown in FIG. 4B, wherein flexible membranes 470 are not illustrated so as to illustrate a means for causing tongues 420, 420A to be displaced from cavities 438, 439. In this exemplary embodiment shown, tongues 420 420A may be tapered to allow easy enter, or exit, of elements 402, 402a into cavities 438, 439, respectively.

Also illustrated in inter vivos tube 500 is insertion point 510 incorporated in an outer surface of H-shaped connector member 401. Insertion point 510 allows entry of a fluid (e.g., air, gas, saline solution, etc.) into the H-shaped connector member 401. Also shown is egress point 520 positioned within a surface of rib 431 separating upper arched segment 403 and lower arched segment 403A of the H-shaped connector 401. Although FIG. 5A illustrated egress point 520 on one side of rib 431, it would be recognized that a similar egress point 520 would exist on the not shown side of rib 431 to enable displacement of tongue 420A to expand element 402A.

In this illustrated case, fluid (or air) injected into insertion point 510 exits the egress points 520 to displace tongues 420 (420A) to increase the circumference of inter vivos tube 500 by increasing the diameter between the arched segments 402, 402A. That is, tongues 420 (420A), when displaced so as to be positioned in an expanded mode, causes the shape of inter vivos tube 500 to be oblong or elliptical rather than a substantially circular shape when tongues 420 (420A) are in an unexpanded state.

Although not shown it would be appreciated, that the insertion point 510 may be incorporated into an end portion of rib 431. In this matter, rib 431 may include a channel that extends from a proximate end to substantially near a distal end of inter vivos tube 500. The channel may be in fluid communication with each of the at least one egress points 520 to allow a fluid (e.g., air, gas, liquid) to be injected into cavities 438, 439.

Although not shown, it would be appreciated that a proximate end and a distal end of H-shaped connector member 401 may be sealed so that cavities 438, 439 may retain a fluid (e.g., air, gas, liquid) injected into cavities 438, 439. Thus, a sealing means (e.g., plugs) may be positioned at a proximate end and a distal end of cavities 438, 439. In this case, as a fluid (e.g., air, gas, liquid) is injected into injection point 510 and exits through egress points 520, cavities 438, 439 become filled with the injected fluid (e.g., air, gas, liquid) and tongues 420, 420A are displaced from cavities 438, 439. Hence, a diameter of the inter vivos tube 500 increases as tongues 420, 420A are displaced from cavities 438, 439, respectively.

Figure 5B:
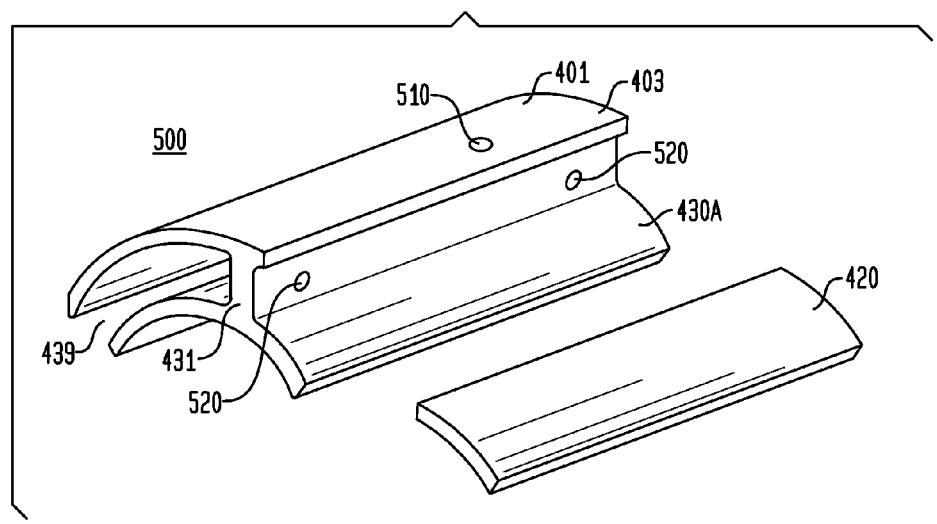

FIG. 5B illustrates prospective view of the exemplary embodiment of the endotracheal tube 500 shown in FIG. 4A (or FIG. 4B), in accordance with the principles of the invention. In this illustrated embodiment, a plurality of egress holes 520 are shown incorporated into rib 471 in order to displace tongues 420, 420A substantially uniformly from cavities 438, 439, respectively.

Figure 6:
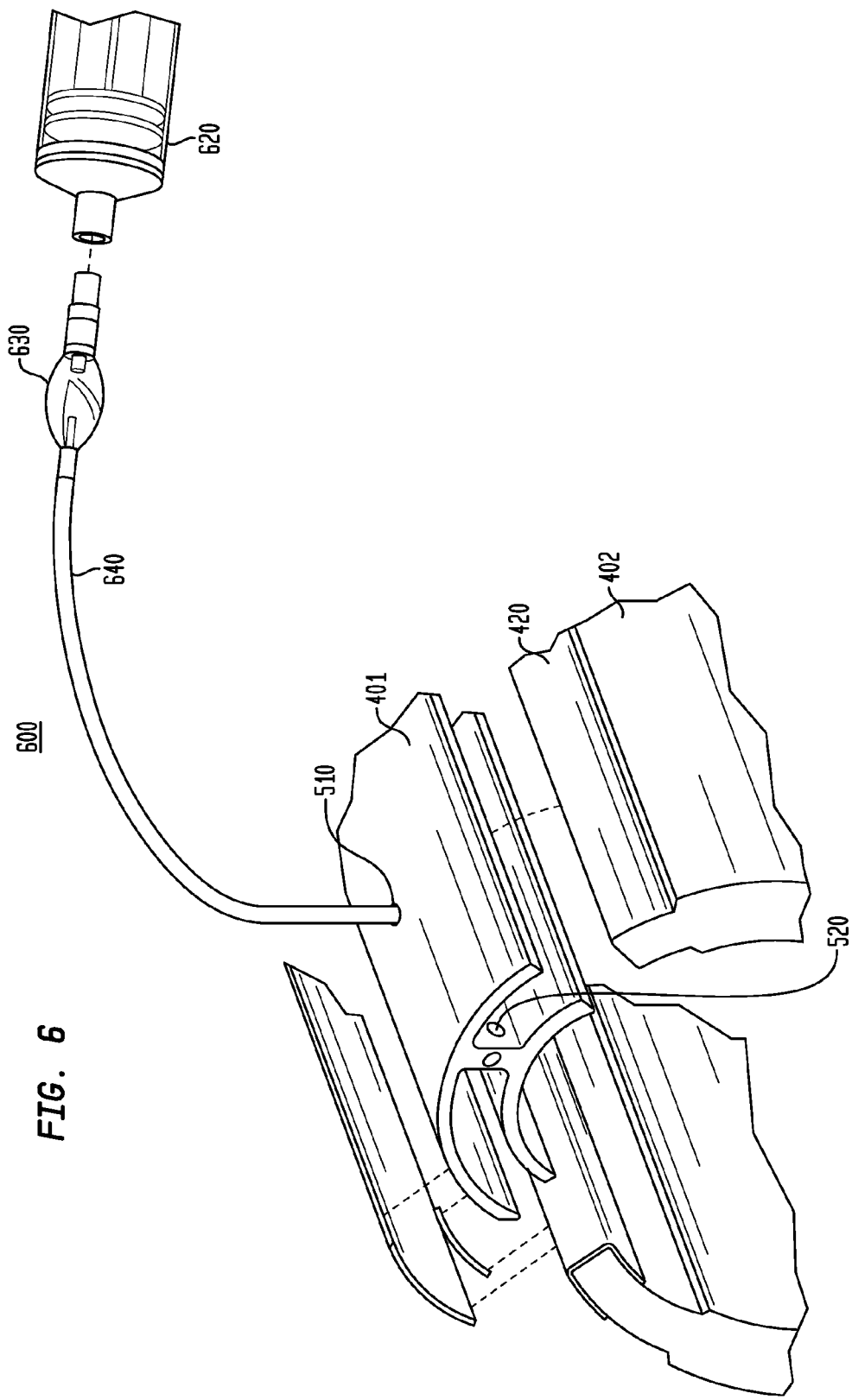
FIG. 6 illustrates a prospective view of a means for causing expansion of the inter vivos tube shown in FIGS. 4A and 4B.

FIG. 6 illustrates prospective view of the exemplary embodiment of the endotracheal tube 600 shown in FIGS. 4A, 4B and 5A, 5B, in accordance with the principles of the invention.

In this illustrated example, a fluid, e.g., air, is injected by a syringe 620, for example, inserted into insertion point 510. The injection process further includes a one-way valve 630 that allows the fluid to pass through tube 640 into H-shaped connection member 401, through injection point 510 and exit egress points 520. The injected fluid displaces tongues 420, 420A, as previously described, to expand the diameter of the inter vivos tube 600. One way valve 630 allows the fluid to pass in a first direction to displace tongues 420, 420A and to statically retain the injected fluid until the valve is released, causing the fluid to exit through insertion point 510.

Figure 7A:
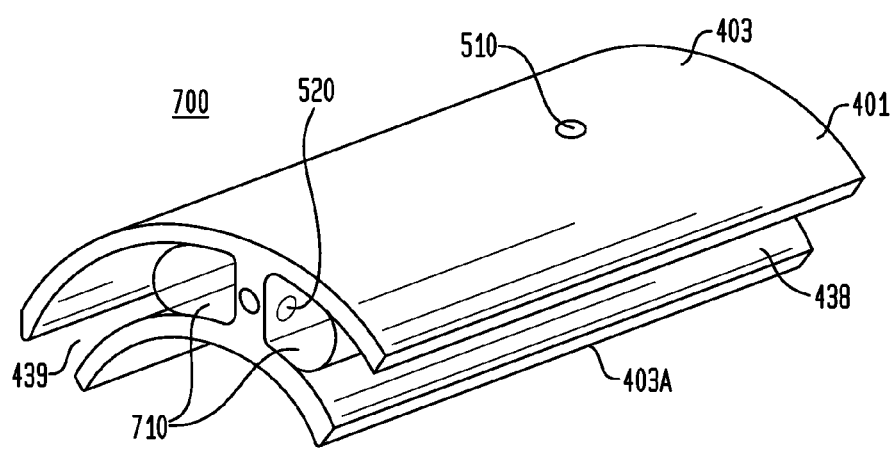
FIGS. 7A and 7B illustrate prospective views of inter vivos tubes in accordance with a second embodiment of the invention.

FIG. 7A illustrates a prospective view of a second aspect of an inter vivos tube 700 in accordance with the principles of the invention. In this exemplary embodiment, balloons or flexible membranes 710 are incorporated into cavities 438, 439. Flexible membranes 710 are in fluid communication with egress holes 520 (not shown) similar to those shown in FIGS. 5A, 5B, to allow fluid to be injected into flexible membrane 710. Flexible membranes 710 when filled expand to partially fill cavity 438, 439 and displace tongues 420, 420A (not shown). Also shown, is injection port 510. As previously discussed, injection port 510 allows entry of an air or fluid into the ribs 431, which is ejected through egress port 520 (not shown). In this case, flexible membranes 710 displace tongues 420, 420A (not shown), to cause inter vivos tube 700 to increase in diameter in a direction substantially perpendicular to arched segment members 402, 402A (not shown).

Figure 7B:
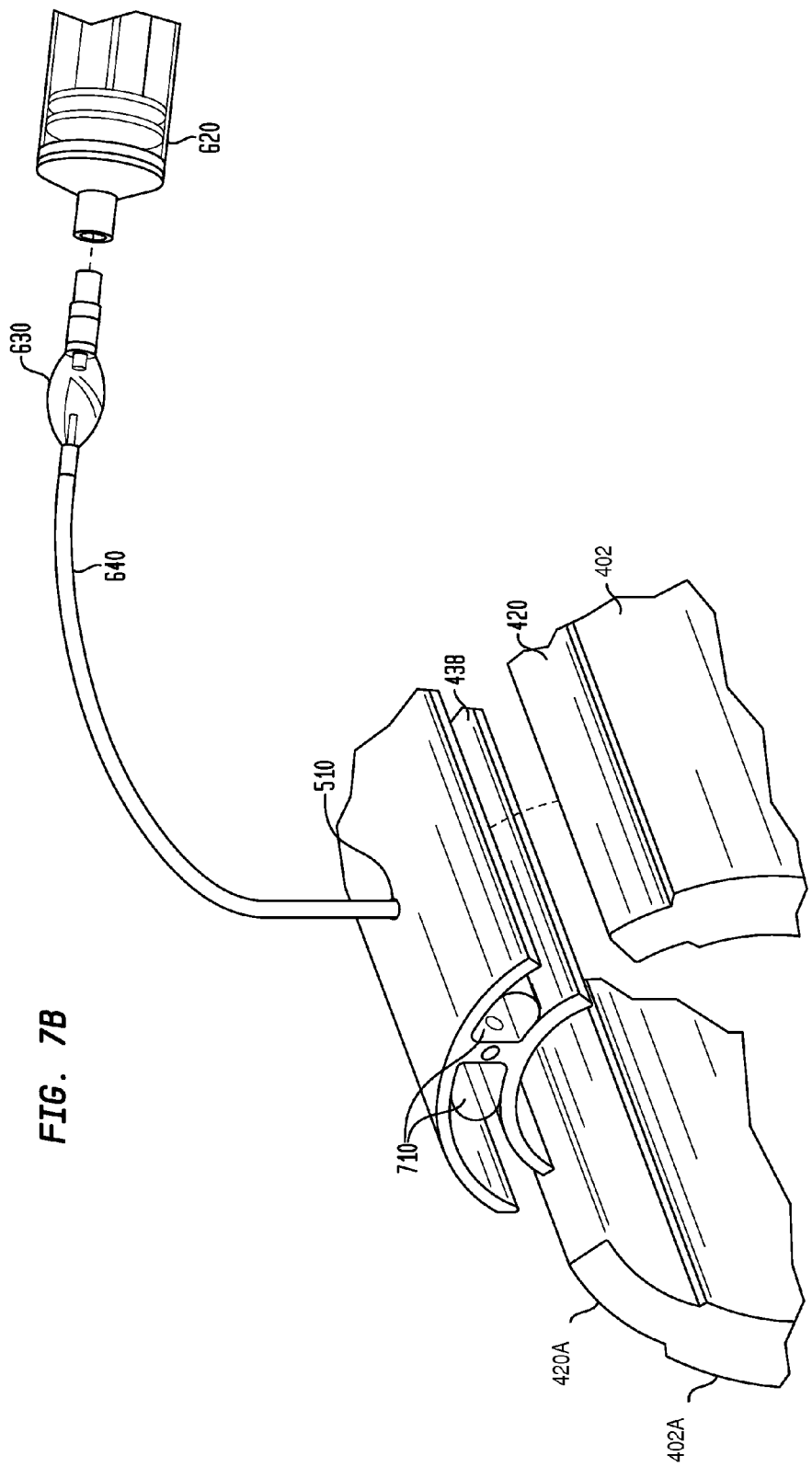

FIG. 7B illustrates a second prospective view of the inter vivos tube 700 shown in FIG. 7A. In this illustrated aspect, the flexible membranes 710 operate as a means to displace the free ends or tongues 420, 420A of arched segment elements 402, 402A from cavities 438, 439. In this case, as flexible membranes 710 expand, by the entry of a fluid through injection point 510, by syringe 620, tongues 420, 420A are displaced from cavities 438, 439 to expand a diameter (and consequentially a circumference) of inter vivos tube 700. Similarly, as the flexible membranes 710 deflate the free ends of arched segments 402, 402A (i.e., tongue 420, 420A) may be returned to cavities 438, 439 so as to reduce the circumference of the inter vivos tube. In this case, the tongues 420, 420A may be returned to cavities 438, 439 by means of the elasticity of the material comprising arched segments 402, 402A.

Figure 8:
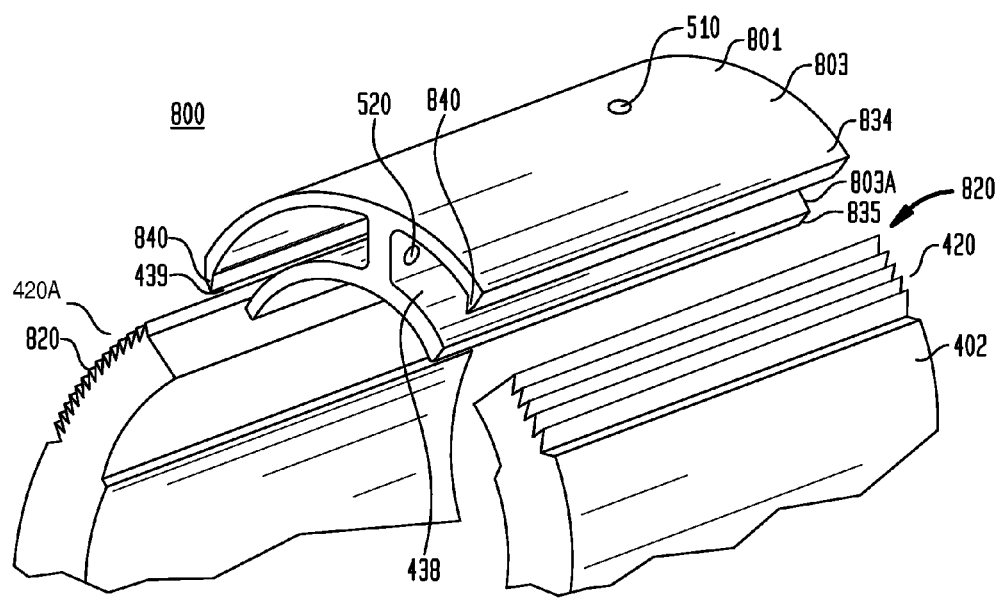
FIG. 8 illustrates a prospective view of an inter vivos tube in accordance with a third embodiment of the invention.

FIG. 8 illustrates a prospective view of an exemplary inter vivos tube 800 in accordance with a second embodiment of the invention. In this illustrated embodiment, H-shaped connector member 801 includes outer arched segment 803 and inner arched segment 803A, which are separated by rib 831. H-shaped connector 810 is similar to H-shaped connector described with regard to FIGS. 4A, 4B, 5A, 5B; hence, a further description of H-shaped connector membrane 801 need not be repeated, again, herein.

In accordance with this second embodiment of the invention, also illustrated, are locking pins 840 positioned on free end 834 of outer arched segment 803 extending into cavities 838, 839. Locking pins 840 restrict the opening of cavities 838, 839 and provide a means for locking tongues 420, 420A into a desired, expanded, position, as will be described.

Also, illustrated in the inter vivos tube 800, is at least one saw tooth or serration 820 on tongue 420 and on tongue 420A. The at least one serration 820 on tongue 420 (420A) is oriented in a direction to allow tongue 420 (420A) to be displaced from cavities 838, 839 and to engage locking pin 840 in order to retain tongue 420 (420A) in a desired position.

Thus, as tongues 420, 420A are displaced from cavities 438, 439 as previously described by the addition of a fluid into cavities 838, 839, the serrations 820 engage retaining point 840 and, thus, retain tongue 420 in an extended position.

In one aspect of the invention, injection point 510 and egress point(s) 520 may be incorporated into H-shaped member 801, as previously described, to provide a means for causing tongues 420, 420A with serrations 820 to be displaced from cavities 438, 439.

In another aspect of the invention, injection point 510 and egress point(s) 520 need not be incorporated into H-shaped connector member 810 and other means for expanding inter vivos tube 800 may be employed.

Although, locking pins 840 are illustrated as being positioned on the outer arched segment 803, it would be appreciated that locking pins 840 may be incorporated onto free end 835 of lower arched segment 803A and the serrations 820 may be positioned on a lower side of tongue 420 (420A) to engage the retaining pin 840 on the lower arched segment 803A, without altering the scope of the invention.

Figure 9A:
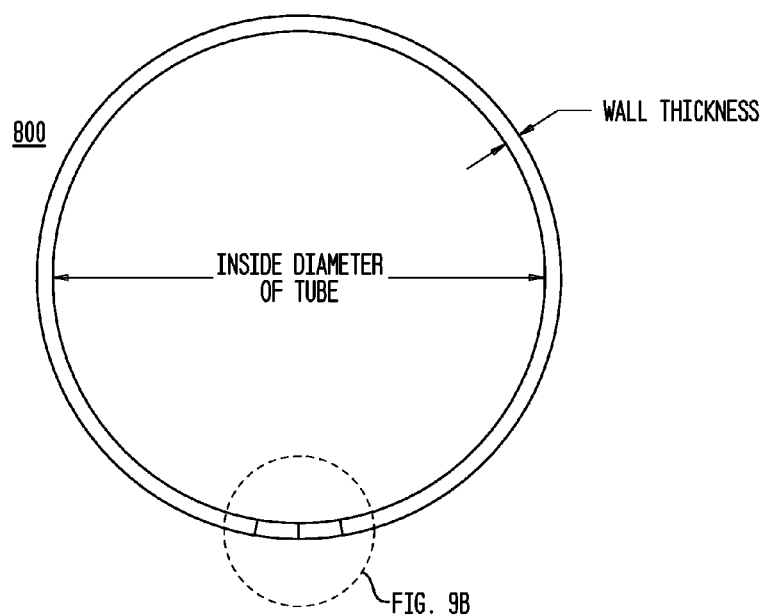
FIGS. 9A and 9B illustrate a cross-sectional view and an expanded cross-sectional view, respectively, of the embodiment of the inter vivos tube shown in FIG. 8.
Figure 9B:
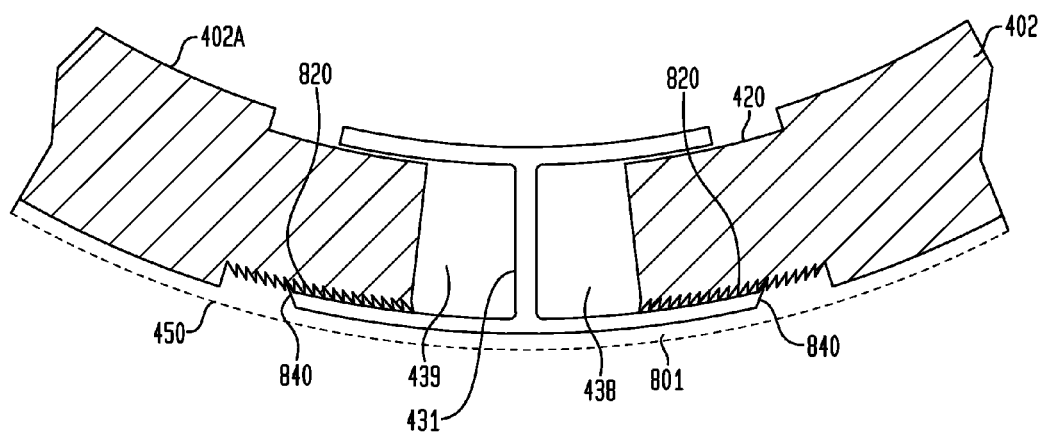

FIG. 9A illustrates a cross section view of inter vivos tube 800 having a known inside, or internal, diameter and a known wall thickness. FIG. 9B illustrates an expanded cross-sectional view of H-shaped connector 801 in accordance with the principles of the invention. In this case, tongues 420, 402A, including serrations 820 are retained in a desired position by engaging the serrations 820 into locking pin 840 as tongues 420, 420A are displaced from cavities 438, 439. In this illustrated embodiment of the invention, as arched segments 402, 402A expand, and tongues 420, 420A are displaced from cavities 438, 439, serrations 820 engage retaining pins 840 to create an elongated diameter substantially perpendicular to arched segments 402, 402A. Accordingly, incremental increases in the diameter of inter vivos tube 800 may be achieved by engaging different ones of the serrations 820. As would be appreciated the incremental increase in the diameter of the inter vivos tube 800 depends on the number and depth of serrations 820.

Figure 10:
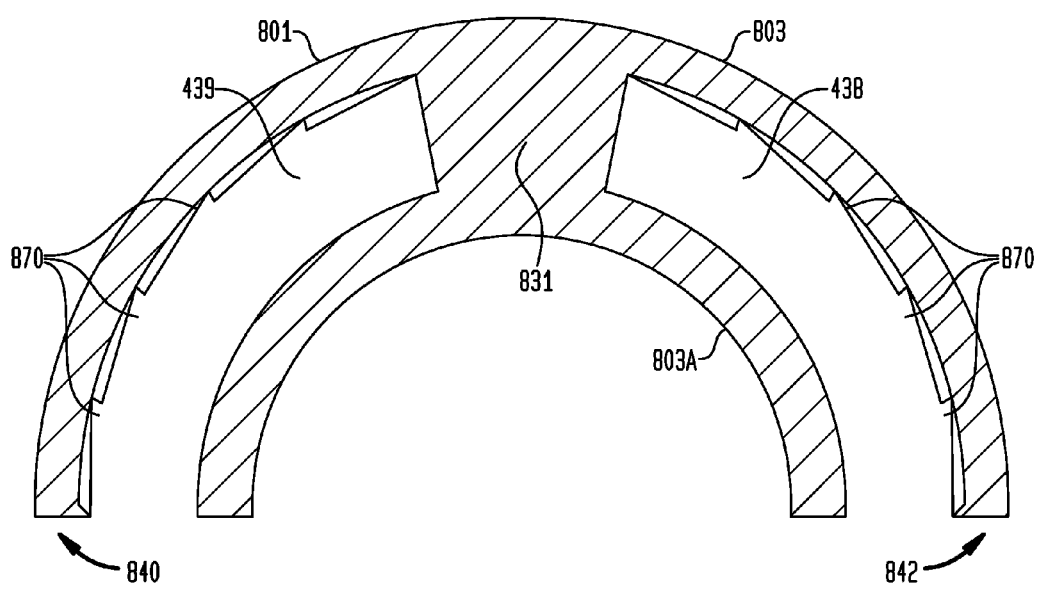
FIG. 10 illustrates a cross-sectional view of another aspect of the inter vivos tube shown in FIG. 8.

FIG. 10 illustrates an expanded cross-sectional view of an exemplary second aspect of the inter vivos tube 800 in accordance with the principles of the invention. In this second aspect of the invention, the inner surfaces of arched outer segment 803 are stepped (870) to prevent displaced tongues 420. 420A (not shown) from being retracted into cavities 438, 439. That is, the steps 870 are oriented opposite to that of serrations 820 so that the steps 870 may engage serrations 820 to prevent arched segments 402, 402A (not shown) from returning to a smaller diameter by the elastic forces of the materials from which segments 402, 402A are composed.

Also shown are retaining pins 840. In one aspect of the invention, the retaining pins 840 may be fixed, while in another aspect of the invention, the retaining pins 840 may be hinged (842) to allow easier displacement of tongues 420 (not shown) from cavities 438, 439. Hinged pins 842 provides a stop to prevent tongue 420, 420A from being retracted into cavities 438, 439 as the hinged pin 842 swings back toward cavity 438, for example, should arched segment 402, 402A (not shown) be contracted (e.g., loss of fluid in cavities 438, 439).

That is, the use of serrations 820 is advantageous as it avoids problems that may be introduced with the inadvertent release of the means for maintaining arched segments 402, 402A in an expanded mode and, thus, causing tongues 402, 402A to reenter cavities 438, 439.

FIG. 11 illustrates an exemplary expander tube element 1100 suitable for providing a means for expanding inter vivos tube 800 in accordance with the principles of the invention.

In this illustrated embodiment of extender tube element 1100, an expandable membrane 1110 surrounds and is fused to tube element 1120 at a distal end 1140 and a proximate end 1130. Within tube member 1120 are at least one egress port 1150. Egress port 1150, in this illustrated embodiment normally would not be visible, unless the expandable membrane 1110 is made of a clear or transparent material. However, egress port 1150 is shown in this illustrated embodiment in order to describe the invention claimed, in sufficient detail to allow one skilled in the art to practice the invention claimed.

A means, e.g., a syringe, (not shown), allows a fluid (e.g., air, gas, liquid) to be injected into tube member 1120 through connector 630, as previously described with regard to FIG. 6. The injected fluid exits through egress holes 1150 and as the injected fluid (e.g., air, gas, liquid) is ejected through egress holes 1150, expandable membrane 1110 expands as the injected fluid fills membrane 1110. As membrane 1110 is fused to tube 1120, the fluid filling the membrane 1110 is retained within the confines of the membrane 1110.

FIG. 12 illustrates an exemplary example of the insertion of expander tube 1100 into inter vivos tube 800, to cause inter vivos tube 800 to expand. In this illustrated example, arched segments 402, 402A (not shown) of inter vivos tube 800 may be expanded as expander tube 1100 is injected with a fluid, as previously described.

The use of the expander tube 1100 is advantageous, as expander tube 1100 may be deflated after the inter vivos tube 800 is expanded (and retained in position by retaining pins 840, as previously described) and the expander tube 1100 may be withdrawn from the expanded inter vivos tube 800 and re-sterilized for future use, if desired.

FIG. 13A illustrates a cross-sectional view of the configuration shown in FIG. 12 wherein expander tube 1100, including extendable membrane 1110 and tube 1120, are inserted within inter vivos tube 800. In this case, inter vivos tube 800 includes two H-shaped members 801 including retaining pins 840, and tongues 420 include serrations 820, as described previously.

In this illustrated embodiment, as fluid is injected into expander tube 1120 and ejected through egress holes 1150, membrane 1110 expands as the fluid is retained in membrane 1110. As membrane 1110 expands, the expanded membrane 1110 pushes against arched segment elements 402, 402A and force tongues 420, 420A (containing serrations 820) to be displaced from cavities 438, 439. As tongues 420, 420A expand, serrations 820 engage retaining pins 840 (842), to retain arch segments 402, 402A, in a desired position.

Figure 13B:
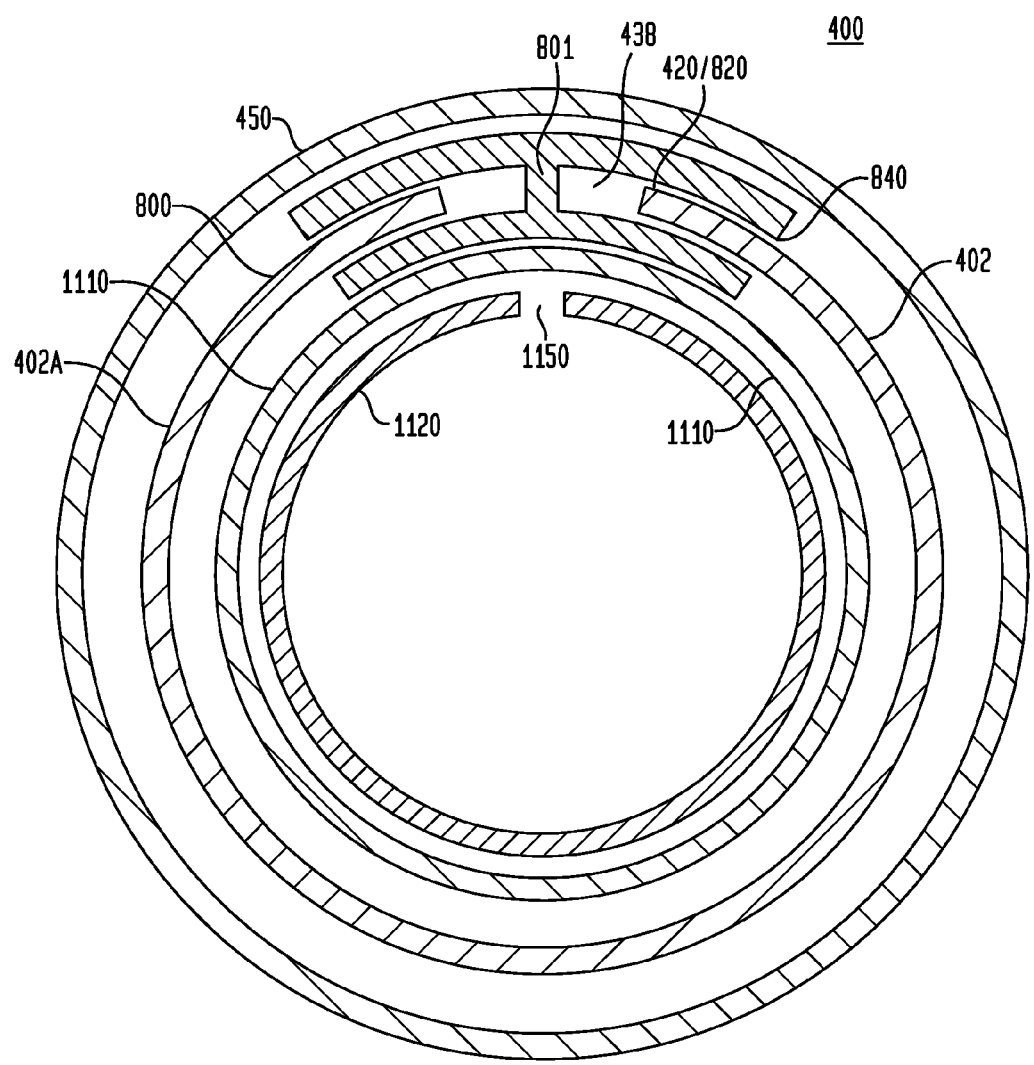

FIG. 13B illustrates a second aspect of the second embodiment of the invention shown in FIG. 13A. In this case, similar to that shown in FIG. 4B, a single H-shaped connector member 801 is incorporated into inter vivos tube 800. Similar to the embodiment described with regard to FIG. 13A, as a fluid expands membrane 1110, arched segments 402, 402A extend and tongues 420, 420A are drawn from cavities 438, 439. Tongues 420, 420A are held in place by retain pin 840 (842) engaging serrations 820 on tongues 420, 420A as previously described.

Figure 14A:
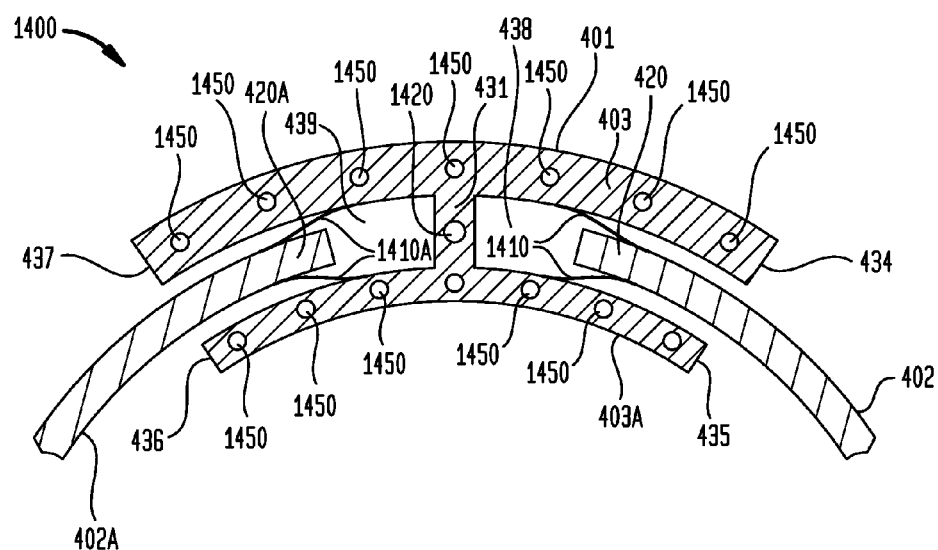
FIG. 14A illustrates a cross section view of the inter vivos tube including a flexible membrane in accordance with one aspect of one embodiment of the invention claimed.

FIG. 14A illustrates another aspect of the present invention. In this illustrative embodiment, the inter vivos tube 1400 includes the H-shaped member 401 formed of an outer arched element 403 and an inner arched element 403A connected at substantially a midpoint of the arched elements 403 and 403A, as previously discussed. Cavities 438 and 439 are formed from the intersection of the rib 432 with the arched elements 403 and 403A. Tongue elements 420 and 420A are slidably insertable into corresponding ones of cavities 438 and 439, as previously described. See for example, FIG. 5A, which describes the relationship between the H-shaped element 401 and the tongue elements 420 and 420A. Although not shown in FIG. 14A, but shown in FIG. 5B, for example, at least one egress port 520 is incorporated into rib 431. Egress port 520 faces into each of cavities 438 and 439.

FIG. 14A further illustrates a flexible membranes 1410 attached to an upper and a lower surface of tongue 420. In one aspect of the invention, the flexible membranes 1410 are attached, as illustrated at a substantially proximal end (i.e., inner edge) of tongue 420. Flexible membranes 1410 are further attached to inner surfaces of the outer circumference member 403 and the inner circumference member 403A. The flexible members 1410 attached to the H-shaped member 401 and the slidable tongue 420 creates a pocket within cavity 438 that retains a fluid (e.g., air, liquid) within cavity 438. In this illustrated example, tongue 420 is shown in an expanded configuration, wherein air, for example, is injected into cavity 438 through egress port 520 (not shown). Similarly, flexible membranes 1410A are attached to an upper and a lower surface of tongue 420A and to corresponding upper and lower surfaces of outer circumference member 403 and 403A creating a pocket similar to that described with regard to cavity 438 within cavity 439.

Flexible membranes 1410 and 1410A are composed of a thin flexible material, such as silicon, that attach to a corresponding tongue 420, 420A. Flexible membrane 1410 (1410A) may be attached to tongue 420 (420A) and inner surfaces of outer circumference member 403 and inner circumference member 403A using a non-toxic adhesive, a heat fusion process, or other similar adhesion methods. In the illustrative example shown, flexible member 1410 and 1410A are attached substantially at a midpoint of corresponding cavities 438, 439. However, it would be appreciated that the flexible membranes 1410, 1410A may be attached along any point of the inner surfaces of outer circumference member 403 and inner circumference member 403A. Attachment of flexible membrane 1410, 1410A to tongues 420, 420A is advantageous as it provides for limited travel of tongues 420, 420A as a fluid is injected into the pockets formed in cavities 438, 439. Although flexible membranes 1410, for example, are shown as two separate membranes, it would be recognized that flexible membrane 1410 may be a single membrane that is attached on one end to a lower (inner) surface of the upper circumference member 403, attached to the upper and lower surfaces of tongue 420, and attached on a second end to an upper (inner) surface lower circumference member 403A.

FIG. 14A further illustrates an ingress port 1420 that is in fluid communication with egress port 520 (shown in FIG. 5B) through a channel (not shown) in rib 431. Ingress port 1420, which is incorporated at one end to the (not shown) channel, includes a sealable material that partially fills ingress port 1420. In this exemplary case, a needle may be used to inject a fluid substantially concurrently into cavities 438, 439 by the needle puncturing the sealable material filling ingress port 1420, discharging air, for example, into the channel and subsequently into the pockets formed in the cavities by the membrane 1410, 1410A and then when the needle is withdrawn, the sealable material in ingress port 1420 seals itself, preventing the injected air from escaping.

Although not shown, it would be recognized that a distal end of H-shaped member 401 and a proximal end of H-shaped member 401 may be sealed so that cavities 438 and 439 are sealed cavities, as previously described. The sealing of cavities 438 and 439 at the proximal end and the distal end of the H-shaped member 401 is advantageous so as to prevent fluid (i.e., air or liquid) from escaping cavities 438 and 439.

In accordance with the principles of the invention, fluid (air, gas, liquid) may be injected through ingress port 1420, which then enters into corresponding cavities 438 and 439. As the fluid enters sealed cavities 438 and 439 (i.e., sealed proximate and distal ends of H-shaped member 401, and flexible membrane 1410, 1410A), the fluid presses against tongues 420, 420A. Tongues 420, 420A slide outward to expand the diameter of the inter vivos tube 1400 in accordance with the principles of the invention.

Figure 14B:
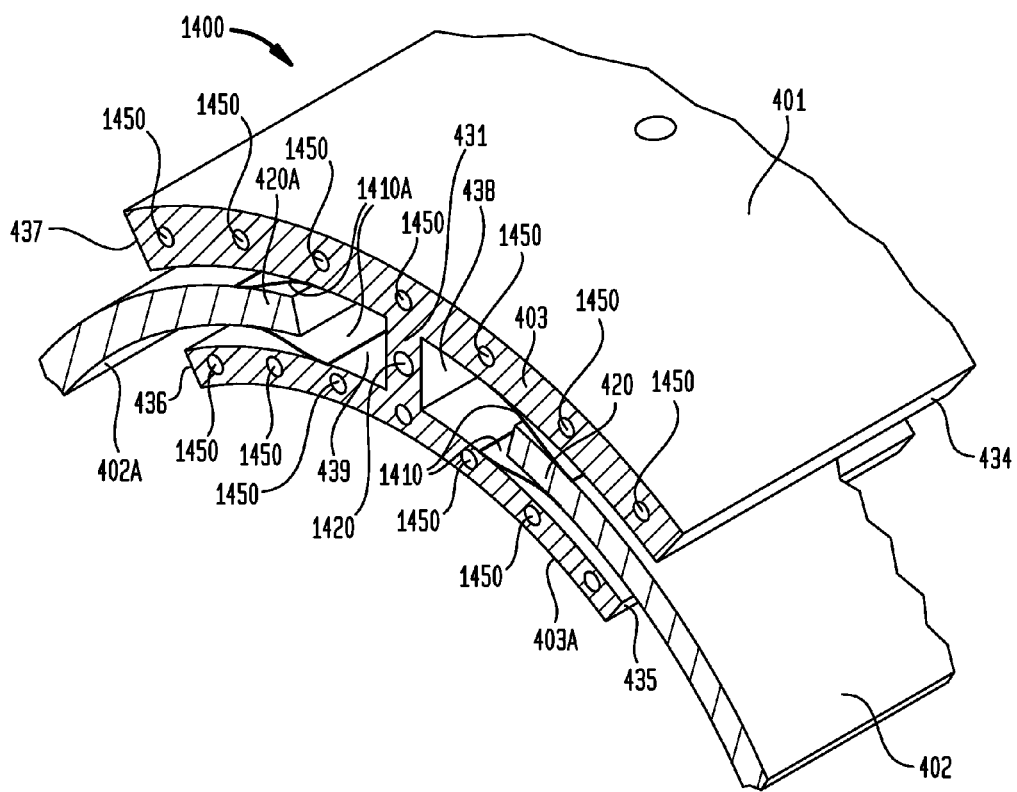
FIG. 14B illustrates a prospective view of the inter vivos tube including a flexible membrane in accordance with the aspect of the invention claimed shown in FIG. 14A.

FIG. 14A illustrates an aspect of an embodiment of the invention wherein the tongues 420, 420A are extended from corresponding cavities 438, 439 to expand the inter vivos tube 1400. FIG. 14B illustrate a prospective view of the aspect of the embodiment of the invention shown in FIG. 14A. In this case, tongues 420, 420A are positioned within corresponding cavities 438, 439 in an extended position such that the inter vivos tube 1400 in accordance with the principles of the invention has an increased diameter.

As would be appreciated, the fluid injected to cavities 438, 439 remains contained within sealed cavities 438, 439 (i.e., FIGS. 14A, 14B) until the fluid is extracted. Extracting of the injected fluid may be performed by inserting a needle point into ingress port 1420 and extracting the fluid (e.g., air). In this case, tongues 420, 420A may slide back into cavities 438, 439, thus, reducing the circumference (i.e., diameter) of the inter vivos tube disclosed, herein.

FIG. 14A further illustrates a plurality of light channels 1450 that may be formed within one of the arched segments 403, 403A. Light channels 1450 represent optically clear channels within H-shaped member 401 to pass light from a proximal end to a distal end of inter-vivos tube 1400. In another aspect of the invention, H-shaped member 401 may be constructed of an optically clear material which may pass light from a proximal end to a distal end of inter-vivos tube 401. Although a plurality of light channel 1450 are shown, it would be appreciated that a single light channel 1450 may be incorporated into the H-shaped member 401 without altering the scope of the invention.

Figure 15A:
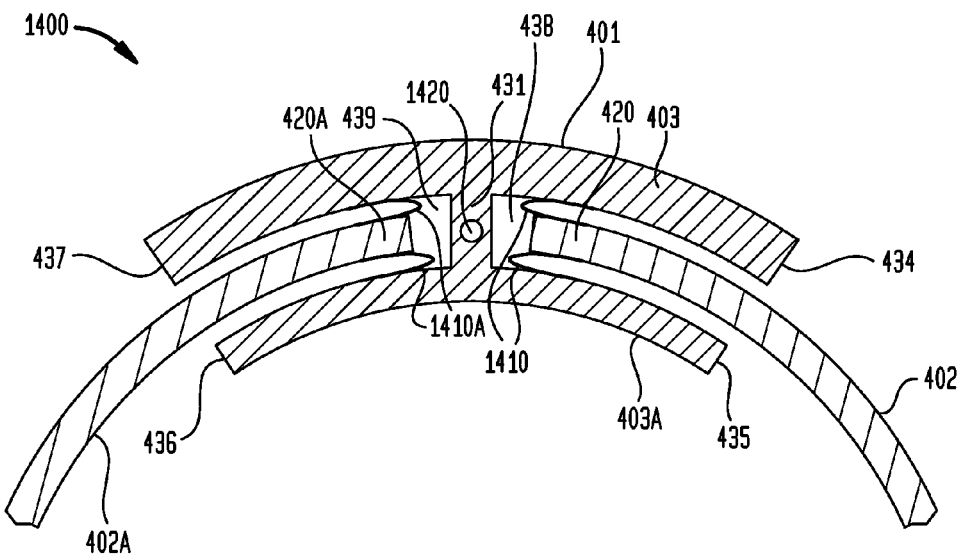
FIG. 15A illustrates a cross section view_of the inter vivos tube including a flexible membrane in accordance with one aspect of a second embodiment of the invention claimed.
Figure 15B:
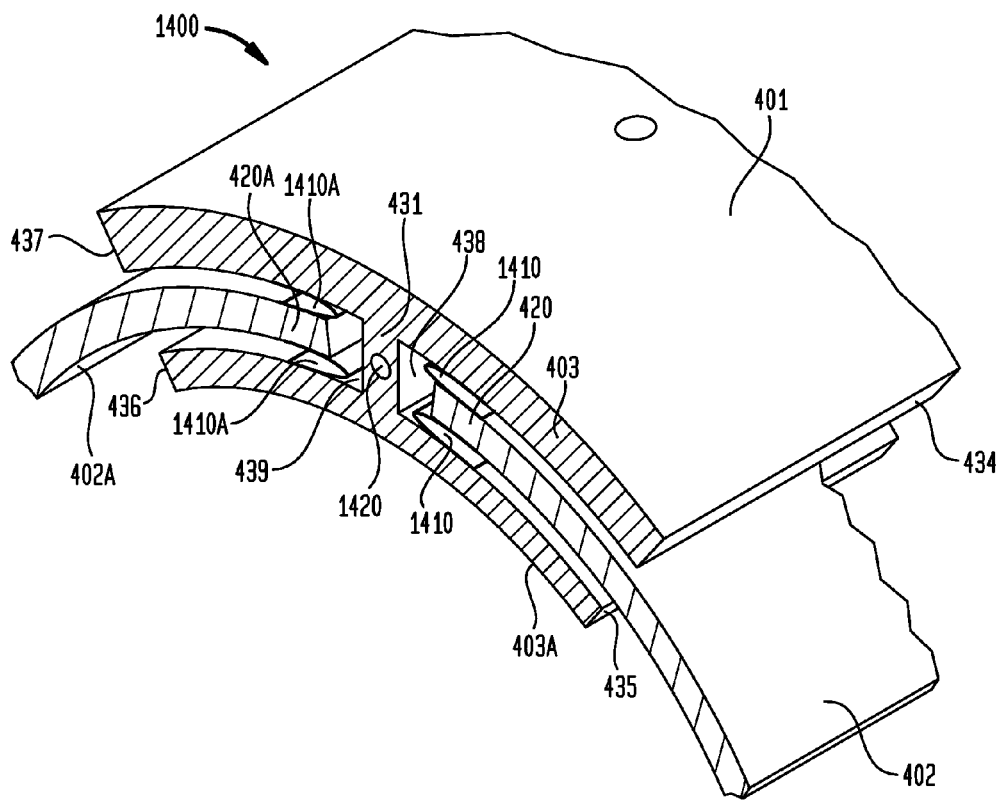
FIG. 15B illustrates a prospective view of the inter vivos tube including a flexible membrane in accordance with the aspect of the invention claimed shown in FIG. 15A.

FIG. 15A illustrates another aspect of the embodiment of an inter vivos tube 1400 shown in FIG. 14A, wherein tongues 420, 420A are positioned within corresponding cavities 438, 439 such that the inter vivos tube 1400 is at a smallest diameter. FIG. 15B illustrates a prospective view of the aspect of the embodiment of the invention shown in FIG. 15A.

Operation of the inter vivos tube shown in FIGS. 14(A and B) and 15 (A and B) is advantageous as the use of sealable material in ingress port 1420 removes the need for valves, typically used to control fluid flow to expand conventional inter vivos tubes (see FIG. 1, FIG. 3). In addition, a single ingress port 1420 allowing air to flow into chambers 438 and 439 is also advantageous as it provides for essentially even distribution of fluid in chambers 438 and 439.

Figure 16:
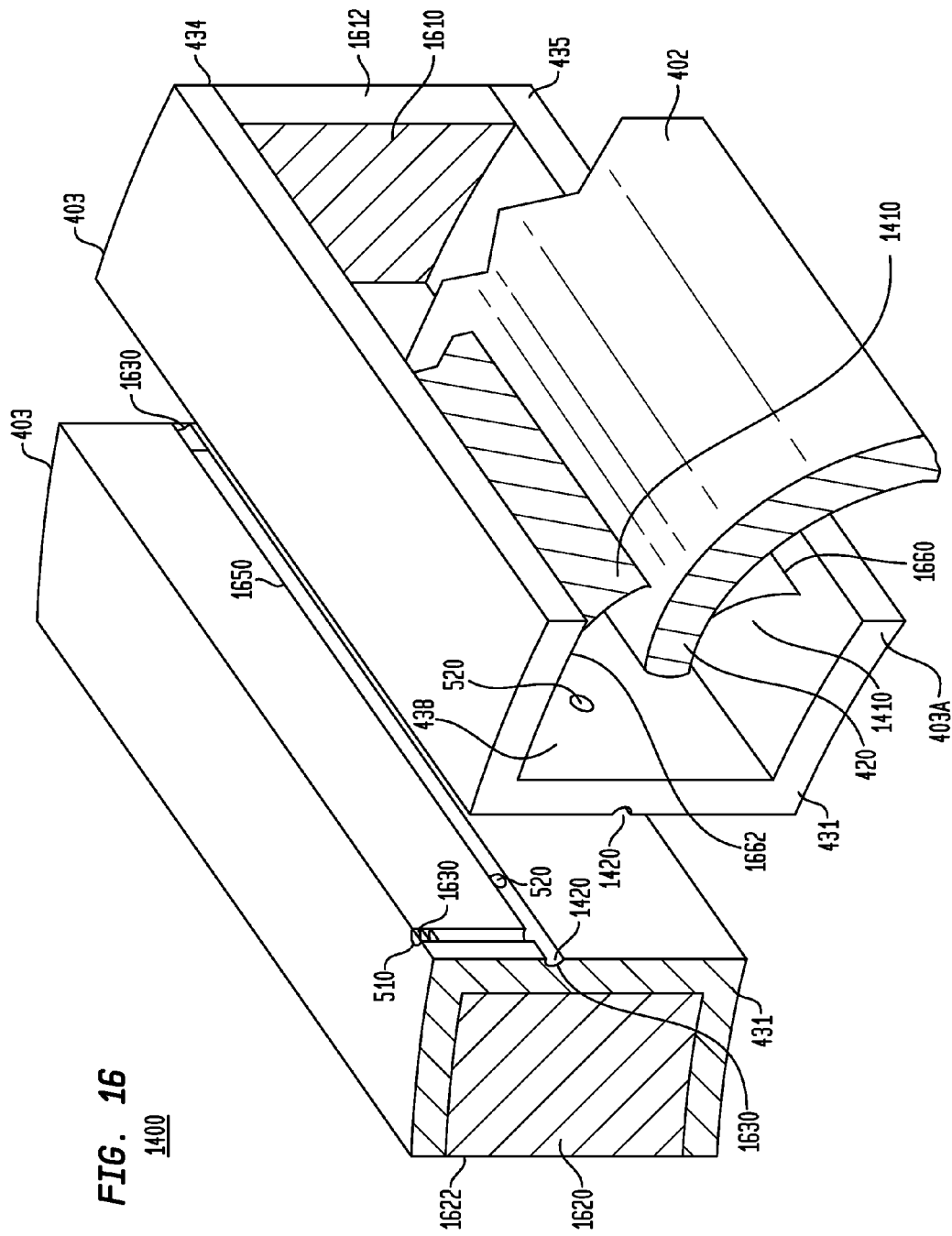
FIG. 16 illustrates an exploded perspective view of the inter vivos tube in accordance with the principles of the invention.

FIG. 16 illustrates a prospective view of inter vivos tube 1400 in accordance with the principles of the invention. In this illustrative embodiment H-shaped member 401 is divided into two separate elements to show the channel 1650 formed in rib 431. Channel 1650 allows fluid communication between ingress point 1420 and egress port 520. In another aspect of the invention, which has been discussed and shown in FIG. 5A, 5B, channel 1650 may be in fluid communication with ingress port 510 (see FIG. 5A, for example). Hence, in accordance with the principles of the invention, the inter vivos tube 1400, shown in FIG. 16, may include one or both of ingress ports 510 and 1420. In addition, in one aspect of the invention, ingress ports 510 and 1420 may be partially filled using a sealable material 1630. Sealable material 1630 allows for the injection of fluid (e.g., air) into channel 1650 and further prevents leakage of the injected fluid from escaping. In another aspect of the invention ingress port 510/1420 may have inserted therein a tubing, similar to that shown in FIG. 6, for example (i.e., tube 640), wherein a syringe 620 may be used to deliver air into sealed chambers 438, 439. Similarly, a valve 630 may be utilized to retain the air injected into the sealed chambers 438, 439. In addition, although ingress port 510 is shown on an outer surface of the upper arched segment 403 of the H-shaped element 401, it would be recognized that ingress port 510 may similarly be incorporated on the outer surface (i.e., concave side) of the lower arched segment 403A of the H-shaped element 401.

Also shown are sealing elements 1610 and 1620. Sealing element 1610 is incorporated into a distal end of each of cavities 438 and 439 (although sealing element 1610 at the distal end of cavity 439 is not shown) in order to seal a distal end of inter vivos tube 1400. Sealing element 1620 is incorporated into a proximal end of each of cavities 438 and 439 (although sealing element 1620 at the proximal end of cavity 438 is not shown) in order to seal a proximal end of inter vivos tube 1400. Sealing elements 1610 and 1620 may be a flexible material, such as silicon, that may be inserted into corresponding cavities (i.e., plugs). Alternatively, sealing elements 1610 and 1620 may represent a flexible or non-flexible material that is attached to the proximal end and the distal end of inter vivos tube 1400 to seal corresponding cavities 438, 439.

Alternatively, sealing elements 1610 and 1620 may be integrally formed at the distal and proximal end, respectively, of inter vivos tube 1400.

In one aspect of the invention, flexible membrane 1410, may be attached, for example, to the inner surfaces of the outer circumference member 403 and the inner surface of the inner circumference member 403A and to the surfaces 1612, 1622 of corresponding sealing elements 1610 and 1620, respectively, to seal cavity 438 such that fluid injected into cavity 438 is retained within cavity 438. In this illustrated example, flexible membrane 1410 is attached along an inner surface of outer circumference member 403 at 1662 and along an inner surface of the inner circumference member 403A at 1660. Similarly, and not shown, flexible membrane 1410A (see FIG. 14A) may be attached to the inner surfaces of outer circumference member 403 and the inner surface of inner circumference member 403A (forming cavity 439) and to the surfaces 1612, 1622 of corresponding sealing elements 1610, 1620, respectively to retain fluid injected into cavity 439.

Referring back to FIG. 5A, a fiber optic channel 471 may be incorporated into rib 431. In a similar manner, as shown in FIG. 14A, one or more fiber optic channels 1450 may be incorporated into rib 431 or one or both of arch segments 403 and 403A. Incorporation of fiber optic channels 1450 in the H-shaped member 401 is advantageous as the fiber optic channels allow the distal end of the inter vivos tube 1400 to be illuminated. In another aspect of the invention, the H-shaped member 401 may be composed of an optical quality material. In this case, the H-shaped member 401 acts as a fiber optic cable that enables light, entering a proximal end of the inter vivos tube 1400 to be distributed at the distal end of the inter vivos tube 1400.

In one aspect of the invention, a channel may be formed within the H-shaped member 401 and a fiber optic cable may be inserted in order to provide illumination as the inter vivos tube 1400 is inserted. In another aspect of the invention, a fiber optic cable may be inserted into channel 1650 as the inter vivos tube 1400 is inserted, through (unsealed) ingress port 510/1420. The fiber optic cable may then be removed in order to provide a clear channel into which air or fluid may be injected.

Figure 17:
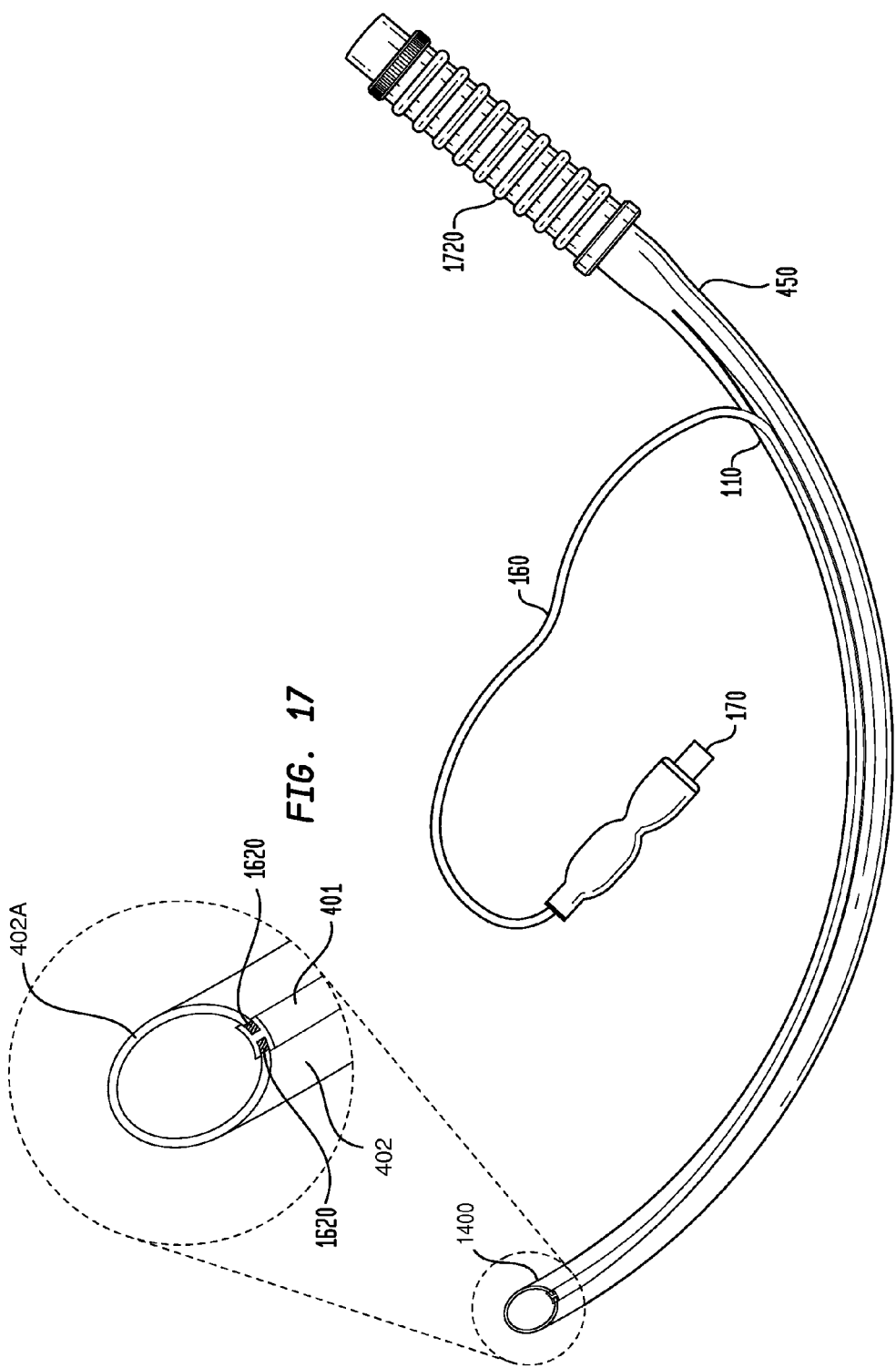
FIG. 17 illustrates an application of an inter vivos tube in accordance with the principles of the invention.

FIG. 17 illustrates an application of an inter-vivos tube 1400 in accordance with the principles of the invention. In this illustrated example, inter vivos tube 1400 is contained within an, optional, condom 450 that provides a smooth outer surface to inter vivos tube 1400. A connection member 170 may be used to deliver a fluid (e.g., air) through tube 160 to ingress port 1420 (not shown) to expand the inter-vivos tube 1400 as discussed.

FIG. 17 further illustrates a close-up view of a distal end of the inter-vivos tube 1400 wherein plugs 1620 (or a similar sealable member) seal the distal end such that cavities 438, 439 are sealed.

As would be recognized, after the inter-vivos tube has been properly expanded, a gas or air may be delivered to a patient through an accordion type connector 1720.

Alternatively, a proximal end of inter-vivos tube 1400 may include ingress port 1420 to expand inter-vivos tube 1400 by inserting a needle into a sealable material within port 1420. After inter-vivos tube 1400 is expanded, an accordion type connector 1720 may be attached to the proximal end of inter-vivos tube 1400 to allow gas to flow through the expanded inter-vivos tube 1400.

Figure 18:
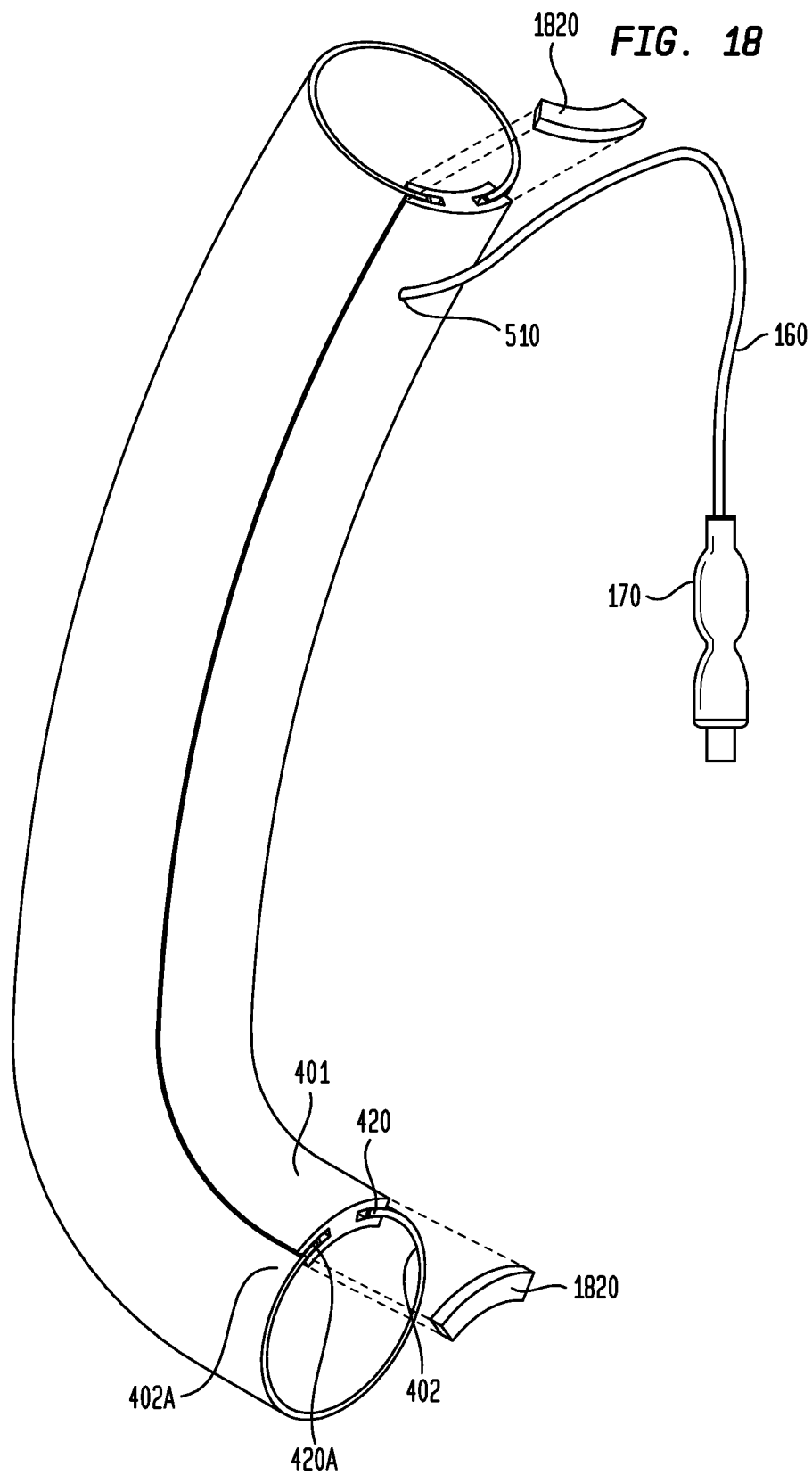
FIG. 18 illustrates an application of an inter vivos tube in accordance with the principles of the invention.

FIG. 18 illustrates another exemplary embodiment of an inter-vivos tube 1400 in accordance with the principles of the invention.

In this illustrated embodiment caps 1820 may be applied to a distal end and a proximal end of the H-shaped member 401 to seal cavities 438, 439. The caps 1820 may be applied to the distal end and proximal end by a non-toxic adhesive or by heat fusion process. In one aspect of the invention, caps 1820 may be an integral part of H-shaped member 401, wherein the caps 1820 are formed onto the ends of the H-shaped member 401. For example, edges of H-shaped member 401 may be pinched, such that the ends of the H-shaped member are drawn and fused together, forming a sealed end. With the incorporation of flexible membranes 1410, 1410A, attached to tongues 420, 420A (see FIG. 14A, for example), fluid injected into cavities 438, 439 may be retained, as previously disclosed.

Although the flexible membrane 1410 (1410A) is shown as being loosely positioned within a corresponding cavity, it would be recognized that the flexible membrane 1410 (1410A) may be composed of a material having sufficient stretchability such that when attached to the corresponding tongue 420, 420A that the travel of tongues 420 and 420A is limited. The stretchability of the flexible member 1410 (1410A) is selected such that the tongues 420, 420A may be positioned substantially close to the surface of rib 431, when the inter vivos tube 1400 disclosed is in a closed (minimum diameter) configuration and only extend to an outer edge (e.g. 436) of the H-shaped element 401 (maximum diameter).

Figure 19A:
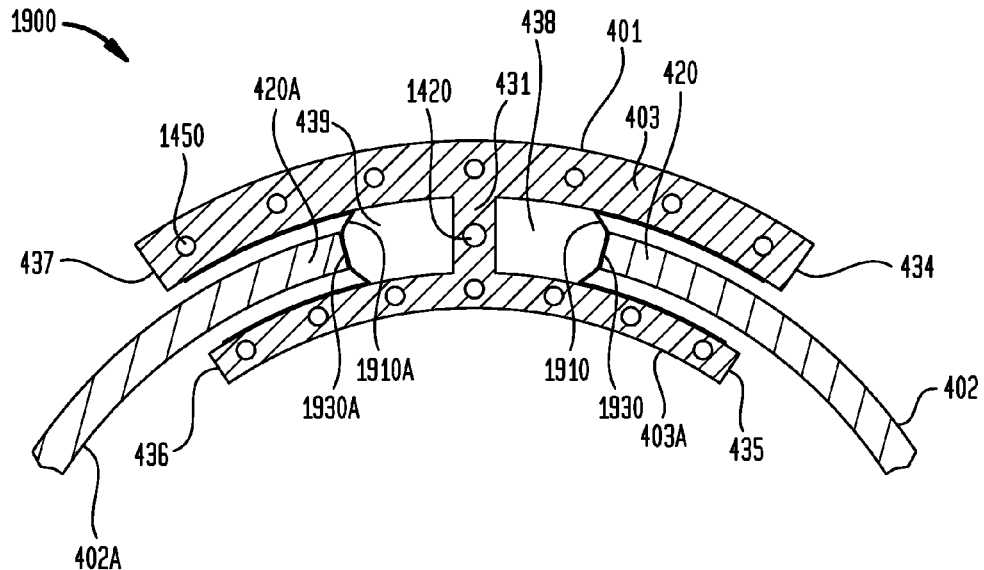
FIG. 19A illustrates a cross section view of the inter vivos tube including a flexible membrane in accordance with one aspect of an embodiment of the invention claimed.

FIG. 19A illustrates a cross-section view of an inter vivos tube 1900 in accordance with another embodiment of the invention. In this illustrated embodiment, the inter vivos tube 1900 is composed on a H-shaped member 401, forming cavities 438 and 439, into which tongues 420, 420A are slidably inserted, similar to that previously described (see FIG. 4A, for example). FIG. 19A illustrates an embodiment similar to that shown in FIG. 14A, wherein the tongues 420, 420A are extended from the cavities 438, 439, respectively, as a fluid (e.g., air) is introduced into cavities 438, 439.

In this illustrated embodiment, a flexible membrane 1910, 1910A is attached to a lower (inner) surface of the upper arched segment 403 of the H-shaped member 401 and to an upper (inner) surface of the lower arched segment 403A of the H-shaped member 401 in respective cavities 438, 439. The attachment of the flexible member 1910, 1910A to the inner surfaces of lower and upper arched segments 403, 403A, is similar to that described with regard to FIG. 14A. In addition, the flexible member 1910, 1910A is attached to an end surface 1930, 1930A of corresponding tongues 420, 420A, respectively. In this case, similar to that described with regard to FIG. 14A, an air-tight cavity may be formed between rib 431 and flexible member 1910, 1910A, for example.

As shown, flexible member 1910, 1910A may be attached along the lower and upper surfaces of arched segments 403, 403A, respectively, from substantially a mid-point of the upper and lower arched segments 403, 403A to an end of the arched segments 403, 403A. Alternatively, flexible member 1910, 1910A may be attached along the lower and upper surfaces of arched segments 403, 403A from substantially a mid-point of the upper and lower arched segments 403, 403A to rib 431 (not shown). As would be appreciated, the length of flexible member 1910, 1910A between the attachment point on the upper and lower arched segments 403, 403A and the end surface 1930, 1930A of tongue 420, 420A, respectively, determines a length of travel of tongues 420, 420A.

Figure 19B:
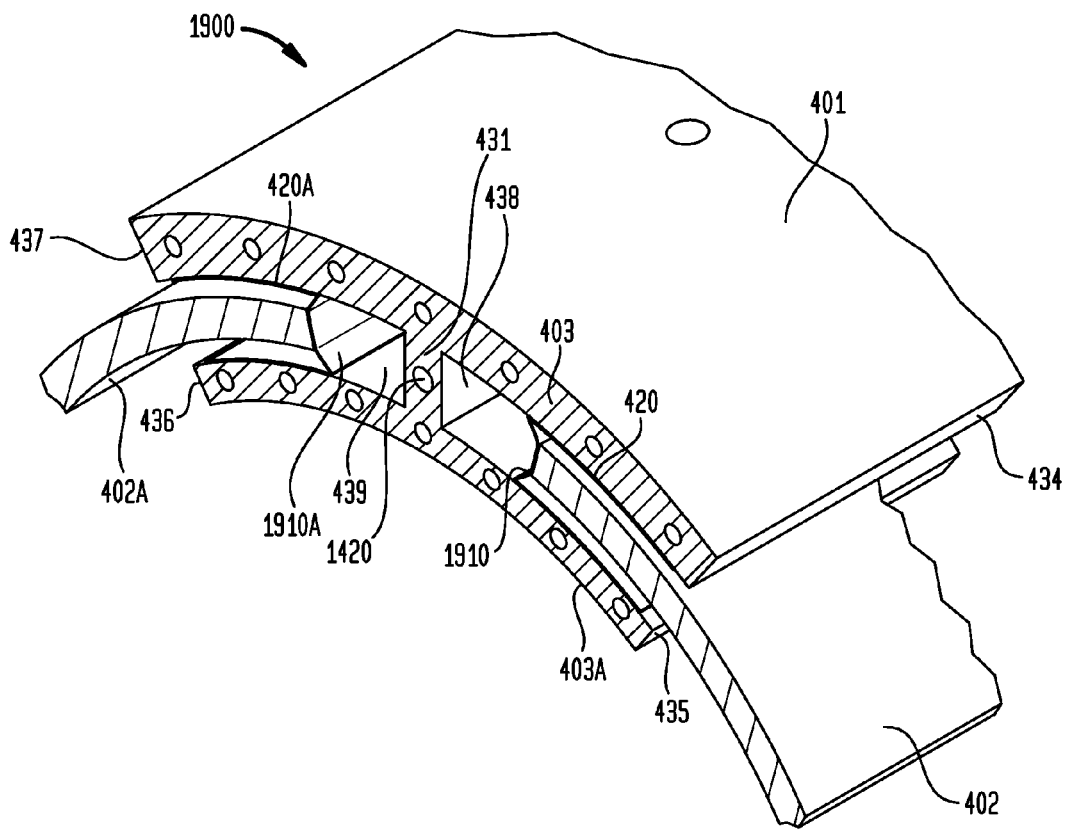
FIG. 19B illustrates a prospective view of the inter vivos tube including a flexible membrane in accordance with the aspect of the invention shown in FIG. 19A.

FIG. 19B illustrates a prospective view of the embodiment of the invention shown in FIG. 19A, wherein tongues 420, 420A are shown in an expanded position.

Figure 20A:
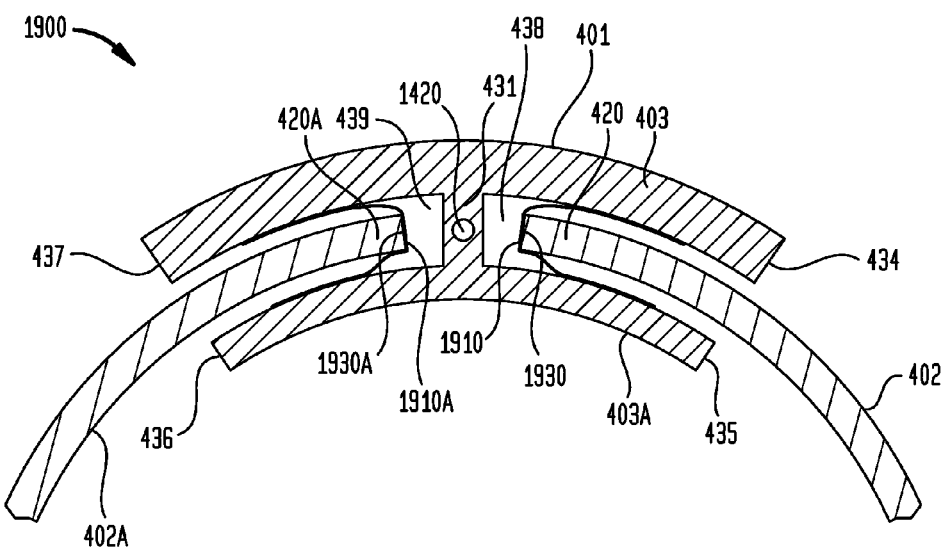
FIG. 20A illustrates a cross section view of the inter vivos tube including a flexible membrane in accordance with an aspect of another embodiment of the invention claimed.

FIG. 20A illustrates another aspect of the inter vivos tube 1900 shown in FIG. 19A, wherein tongues 420, 402A are inserted into cavities 438, 439, respectively. In this illustrated aspect, flexible member 1910, 1910A are shown stretched around or enveloping end surfaces 1930, 1930A of tongues 420, 420A, respectively.

Although, tongues 420, 420A are shown separated from rib 431, in this contracted position, it would be appreciated that the unattached portion of flexible member 1910, 1910A may have a length (or be sized) such that the end surface 1930, 1930A of tongue 420, 420A, respectively, is substantially near rib 431 to provide a minimum diameter inter vivos tube 1900 in the contracted position. Similarly, the length of the unattached portion of flexible member 1910, 1910A determines the length of travel of tongues 420, 420A and the maximum diameter of inter vivos tube 1900 in the expanded position. Preferable, the free end of the unattached portion of flexible membrane 1910, 1910A begins at substantially a mid-point of the upper and lower arched segments 403, 403A and the length of the unattached portion of the flexible membrane is sized so that tongues 420, 420A are substantially near rib 431 in the contracted position and expand an edge of cavities 438, 439 in the expanded position.

Although flexible membranes 1900, 1910A are shown as one piece extending from a lower surface of upper arched member 403 to an upper surface of lower arched member 403A, it would be appreciated that membranes 1900, 1910A may be composed of two pieces; one extending from a lower surface of upper arched member 403 to end surface 1930, 1930A of tongue 420, 420A, respectively, and a second one extending from an upper surface of lower arched member 403A to end surface 1930, 1930A of tongues 420, 420A, respectively.

Figure 20B:
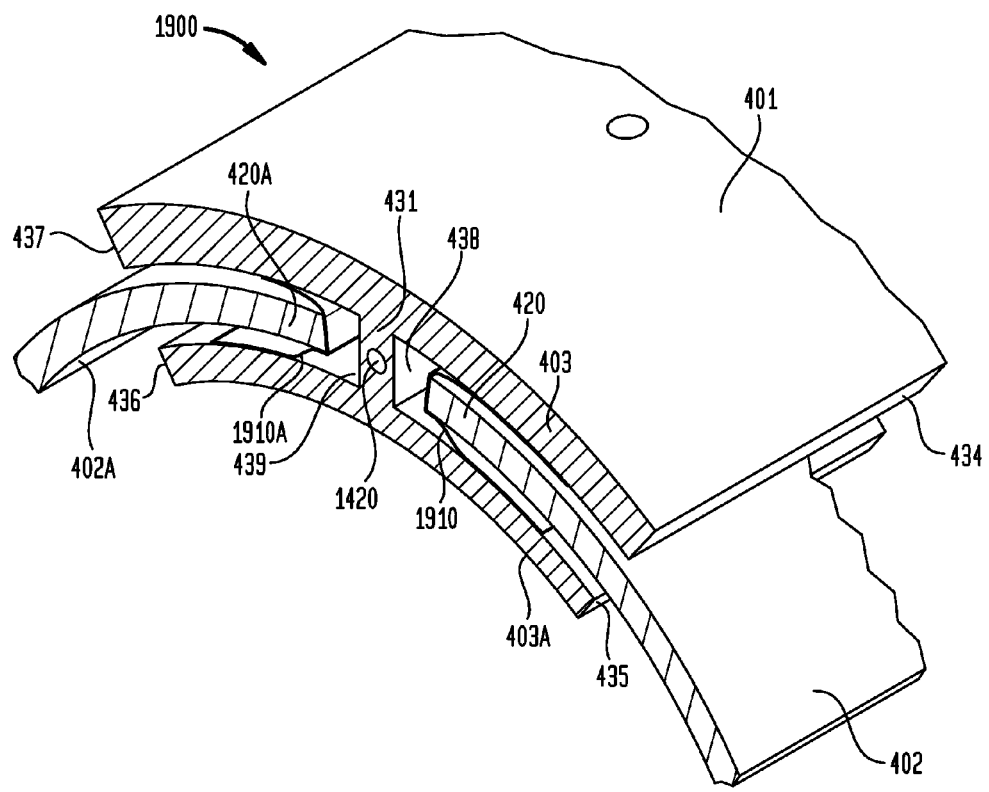
FIG. 20B illustrates a prospective view of the inter vivos tube including a flexible membrane in accordance with the aspect of the invention shown in FIG. 20A.

FIG. 20B illustrates a prospective view of the embodiment of the invention shown in FIG. 20A, wherein tongues 420, 420A are in a contracted position.

Although the invention has been described with regard to preferred embodiments of the invention claimed, it is expressly intended that all combinations of those elements that perform substantially the same function in substantially the same way to achieve the same results are within the scope of the invention. Substitutions of elements from one described embodiment to another are also fully intended and contemplated.

The terms "a" or "an" as used herein are to describe elements and components of the invention. This is done merely for convenience and to give a general sense of the invention. The description herein should be read to include one or at least one and the singular also includes the plural unless indicated to the contrary.

The term "comprises", "comprising", "includes", "including", "as", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

What is claimed is:

1. An expandable inter vivos tube comprising:
   a flexible member extending longitudinally substantially along an edge of said inter vivos tube, said flexible member comprising:
   an outer circumference member;
   an inner circumference member; and
   a rib element connecting said outer circumference member and said inner circumference member at substantially a midpoint of said outer circumference and said inner circumference member, said outer circumference member, said inner circumference member and said rib member forming a first cavity and a second cavity, respectively,
   a channel formed in said rib element, said channel extending from a proximal end to substantially a distal end of said rib element,
   sealing elements sealing a proximal end and a distal end of each of said first cavity and said second cavity;
   a flexible longitudinal tube member having a first free end and a second free end, said first free end and second free end slidably engaging said flexible member in a corresponding one of said first cavity and said second cavity;
   a first flexible membrane within said first cavity, said first flexible membrane attached, on a first end, to an inner surface of said outer circumference member and to a surface of said first free end; and
   a second flexible membrane within said second cavity, said second flexible membrane attached, on a first end, to an inner surface of said outer circumference member and to a surface of said second free end.

2. The inter vivos tube of claim 1, further comprising:
   an injection port in fluid communication with said channel, said injection port being positioned at one of said proximal end of said rib member and a proximate end of said outer circumference member; and
   at least one egress port in fluid communication through said channel with said injection port, said at least one egress port positioned within a surface of said rib element facing a corresponding one of said first cavity and said second cavity.

3. The inter vivos tube of claim 2, wherein said injection port is sealed with a sealable material.

4. The inter vivos tube of claim 1, wherein said first free end and said second free end are tapered.

5. The inter vivos tube of claim 1, further comprising:
   a third flexible membrane within said first cavity, said third flexible membrane attached, on a first end, to an upper surface of said inner circumference member and to a surface of said first free end; and
   a fourth flexible membrane within said second cavity, said fourth flexible membrane attached, on a first end, to an upper surface of said inner lower circumference member and to a surface of said second free end.

6. The inter vivos tube of claim 5, where said first and third flexible membranes are a single membrane and said second and fourth membranes are a single membrane.

7. The inter vivos tube of claim 5, wherein said surface of a corresponding one of said first free end and said second free end is one of: a lower surface and an end surface.

8. The inter vivos tube of claim 5 wherein said third flexible membrane is attached along said upper surface of said inner circumference member substantially at a midpoint of said inner circumference member.

9. The inter vivos tube of claim 1, wherein said surface of a corresponding one of said first free end and said second free end is one of: an upper surface and an end surface.

10. The inter vivos tube of claim 1, wherein corresponding one of said first flexible and said second membrane are attached along said inner surface of said outer circumference member of a corresponding one of said first cavity and said second cavity substantially at a midpoint of said outer circumference member.

11. An inter vivos tube comprising:
a longitudinal H-shaped member comprising:
   an arched outer member;
   an arched inner member;
   a rib member connecting, at a substantial mid-point, said arched outer member and said arched inner member, said arched outer member, said arched inner member and said rib member forming a first cavity and a second cavity, respectively,
   a channel formed in said rib member, said channel extending from a proximal end of said rib member,
sealing members sealing a proximal end and a distal end of said inter vivos tube;
a flexible tube comprising a first free end and a second free end, said first free end slidably engaging said first cavity and said second free end slidably engaging said second cavity;
a first flexible membrane attached, at a first end, to an inner surface of said arched outer member of said first cavity and attached to an end surface of said first free end; and
a second flexible membrane attached, at a first end, to an inner surface of said arched outer member of said second cavity and attached to an end surface of said second free end.

12. The inter vivos tube of claim 11, further comprising:
said first flexible membrane being attached, at a second end, to an upper surface of said arched inner member of said first cavity; and
said second flexible membrane being attached, at a second end, to an upper surface of said arched inner member of said second cavity.

13. The inter vivos tube of claim 11, wherein an unattached portion of each of said first flexible membrane and said second flexible membrane is sized to prevent said first free end and said second free end from exiting corresponding said first cavity and said second cavity.

14. The inter vivos tube of claim 11, wherein said first flexible membrane and said second flexible membrane are attached from substantially a midpoint of said inner surface of said arched outer member and arched inner member of corresponding first cavity and second cavity to substantially an open end of corresponding first cavity and second cavity.

15. The inter vivos tube of claim 14, wherein said first flexible membrane and said second flexible membrane are attached from substantially said rib to substantially a midpoint of said inner surface of said arched outer member and arched inner member of corresponding first cavity and second cavity.

16. The inter vivos tube of claim 11 further comprising:
at least one ejection port positioned on a surface of said rib facing into a corresponding one of said first cavity and said second cavity, each of said at least one ejection port being in fluid communication with said channel.

17. The inter vivos tube of claim 11, further comprising:
an injection port being in fluid communication with said channel, said injection port positioned at a proximal end of one of: said rib member, said outer arched member and said inner arched member.

18. The inter vivos tube of claim 11, further comprising:
a sealable material in said injection port.

19. The inter vivos tube of claim 11, further comprising:
a third flexible membrane attached, at a first end, to an inner surface of said arched inner member of said first cavity and attached to said end surface of said first free end; and
a fourth flexible membrane attached, at a first end, to an inner surface of said arched inner member of said second cavity and attached to said end surface of said second free end.

20. An inter vivos tube comprising:
an H-shaped element comprising:
   a first cavity and a second cavity, said first cavity and said second cavity formed by a rib element joining an outer circumference element and an inner circumference element, said rib element further comprising:
   a channel extending from a proximal end to substantially a distal end of said rib element, said proximal end and said distal end of said channel being sealed with a sealable material; and
   at least one egress port on a surface of said rib element, each of said at least one egress port being in fluid communication with said channel and facing a corresponding one of said first cavity and said second cavity,
sealing means for sealing a proximal end and a distal end of each of said first cavity and said second cavity; and
a flexible tube comprising a first free end and a second free end, said first and second free ends slidably engaging a corresponding one of said first cavity and second cavity; and
a first flexible membrane contained in said first cavity, said first flexible membrane being attached:
   on a first end to an inner surface of said outer circumference element,
   on a second end to an inner surface of said inner circumference element, and
   on an end surface of said first free end, and
a second flexible membrane contained in said second cavity, said second flexible membrane being attached:
   on a first end to an inner surface of said outer circumference element,
   on a second end to inner surface of said inner circumference element , and
   on an end surface of said second free end.

* * * * *